US012685477B2

(12) United States Patent
Omer et al.

(10) Patent No.:  US 12,685,477 B2
(45) Date of Patent:  Jul. 21, 2026

(54) APPARATUS AND METHOD FOR ANALYSIS AND MONITORING OF HIGH FREQUENCY ELECTROGRAMS AND ELECTROCARDIOGRAMS IN VARIOUS PHYSIOLOGICAL CONDITIONS

(71) Applicant: BSP Medical Ltd., Tel Aviv-Jaffa (IL)

(72) Inventors: Noam Omer, Rosh HaAyin (IL); Amir Beker, Rosh HaAyin (IL)

(73) Assignee: BSP Medical Ltd., Tel-Aviv-Yafo (IL)

( * ) Notice: Subject to any disclaimer, the term of this patent is extended or adjusted under 35 U.S.C. 154(b) by 304 days.

(21) Appl. No.: 18/278,635

(22) PCT Filed: Feb. 24, 2022

(86) PCT No.: PCT/IL2022/050215
§ 371 (c)(1),
(2) Date: Aug. 24, 2023

(87) PCT Pub. No.: WO2022/180633
PCT Pub. Date: Sep. 1, 2022

(65) Prior Publication Data
US 2024/0138744 A1      May 2, 2024

Related U.S. Application Data

(60) Provisional application No. 63/152,917, filed on Feb. 24, 2021.

(51) Int. Cl.
*A61B 5/366*       (2021.01)
*A61B 5/08*        (2006.01)
*A61B 5/364*       (2021.01)

(52) U.S. Cl.
CPC ............ *A61B 5/366* (2021.01); *A61B 5/0816* (2013.01); *A61B 5/364* (2021.01)

(58) Field of Classification Search
CPC ....... A61B 5/366; A61B 5/0816; A61B 5/364; A61B 5/4884; A61B 5/346
See application file for complete search history.

(56) References Cited

U.S. PATENT DOCUMENTS 8,538,510 B2 *   9/2013  Toledo .................. A61B 5/316
                                                    600/509
8,626,275 B1     1/2014  Amit et al.
                        (Continued)

FOREIGN PATENT DOCUMENTS

EP        2954841 A1    12/2015

OTHER PUBLICATIONS

International Preliminary Report on Patentability Dated Sep. 7, 2023 From the International Bureau of WIPO Re. Application No. PCT/IL2022/050215 (9 Pages).
(Continued)

*Primary Examiner* — Michael J Lau
(74) *Attorney, Agent, or Firm* — Hemisphere Law, PLLC

(57)      ABSTRACT

A method of analyzing a subject's cardiac condition, the method including measuring an ECG or an electrogram signal, extracting a high frequency (HF) portion from a QRS portion of the ECG or electrogram signal, producing a HFQRS signal, calculating a HF value based on analyzing the HFQRS signal, measuring at least one more physiological value associated with the subject, and analyzing the ECG or the electrogram signal based on the HF value and the physiological value. Related apparatus and methods are also described.

19 Claims, 14 Drawing Sheets

(56) References Cited

U.S. PATENT DOCUMENTS

| 2008/0194978 | A1* | 8/2008 | Beker | A61B 5/366 |
| | | | | 600/516 |
| 2011/0040199 | A1* | 2/2011 | Hopenfeld | A61B 5/349 |
| | | | | 600/515 |
| 2019/0038164 | A1* | 2/2019 | Matsuura | A61B 5/352 |
| 2019/0159674 | A1* | 5/2019 | Kogure | G16H 40/67 |
| 2020/0187803 | A1* | 6/2020 | Komatsu | A61B 5/352 |
| 2020/0345058 | A1* | 11/2020 | Bowen | A61K 31/465 |

OTHER PUBLICATIONS

International Search Report and the Written Opinion Dated Jun. 13, 2022 From the International Searching Authority Re. Application No. PCT/IL2022/050215. (18 Pages).

Lipton et al. "High-Frequency QRS Electrocardiogram Analysis During Exercise Stress Testing for Detecting Ischemia", International Journal of Cardiology, XP022441818, 124(2): 198-203, Feb. 29, 2008.

Moody et al. "Derivation of Respiratory Signals From Multi-Lead ECGs", Computers in Cardiology, 12(1985): 113-116, Sep. 8, 1985.

* cited by examiner

200

202

203

204

201

MEASURE AN ECG OR ELECTROGRAM SIGNAL — 402

EXTRACT A HIGH FREQUENCY (HF) PORTION FROM THE ECG OR ELECTROGRAM SIGNAL, PRODUCING A HFQRS SIGNAL — 404

CALCULATE A HF VALUE BASED ON ANALYZING THE HFQRS SIGNAL — 406

MEASURE AT LEAST ONE MORE PHYSIOLOGICAL VALUE ASSOCIATED WITH THE SUBJECT — 408

ANALYZE THE ECG OR THE ELECTROGRAM SIGNAL BASED ON THE HF VALUE AND THE PHYSIOLOGICAL VALUE — 410

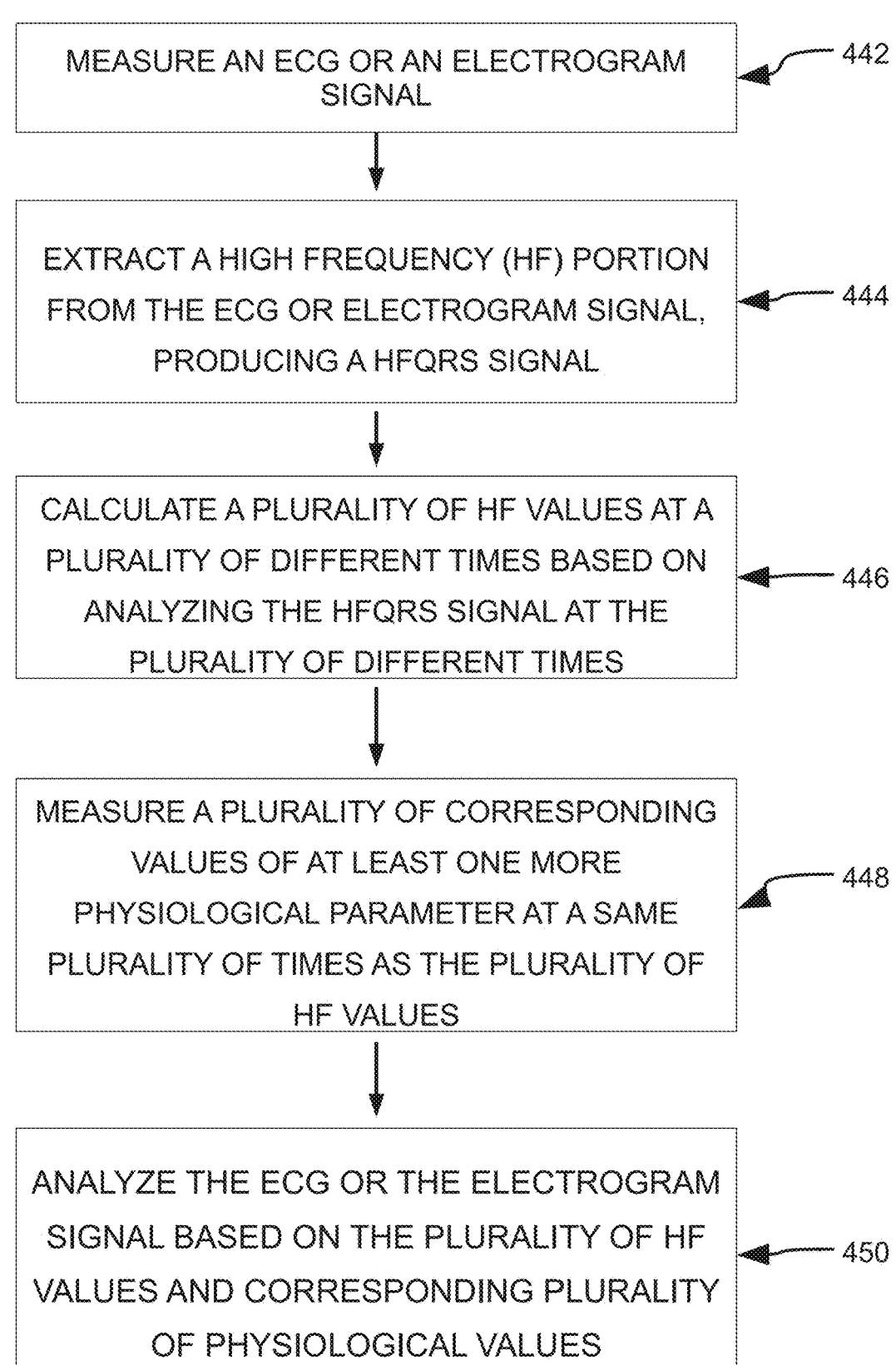

MEASURE AN ECG OR AN ELECTROGRAM SIGNAL — 442

EXTRACT A HIGH FREQUENCY (HF) PORTION FROM THE ECG OR ELECTROGRAM SIGNAL, PRODUCING A HFQRS SIGNAL — 444

CALCULATE A PLURALITY OF HF VALUES AT A PLURALITY OF DIFFERENT TIMES BASED ON ANALYZING THE HFQRS SIGNAL AT THE PLURALITY OF DIFFERENT TIMES — 446

MEASURE A PLURALITY OF CORRESPONDING VALUES OF AT LEAST ONE MORE PHYSIOLOGICAL PARAMETER AT A SAME PLURALITY OF TIMES AS THE PLURALITY OF HF VALUES — 448

ANALYZE THE ECG OR THE ELECTROGRAM SIGNAL BASED ON THE PLURALITY OF HF VALUES AND CORRESPONDING PLURALITY OF PHYSIOLOGICAL VALUES — 450

FIGURE 4C

| Time to Maximal HR [s] | Max HR [BPM] | Relative HR increase [%] | HFQRS at Max HR [μV] | HFQRS index [%] |
|---|---|---|---|---|
| 460 | 108 | 63% | 2.388 | 55% |
| 370 | 102 | 55% | 2.619 | 50% |
| 350 | 97 | 47% | 2.726 | 48% |
| 310 | 91 | 38% | 3.355 | 36% |
| Baseline | 66 | - | 5.262 | - |

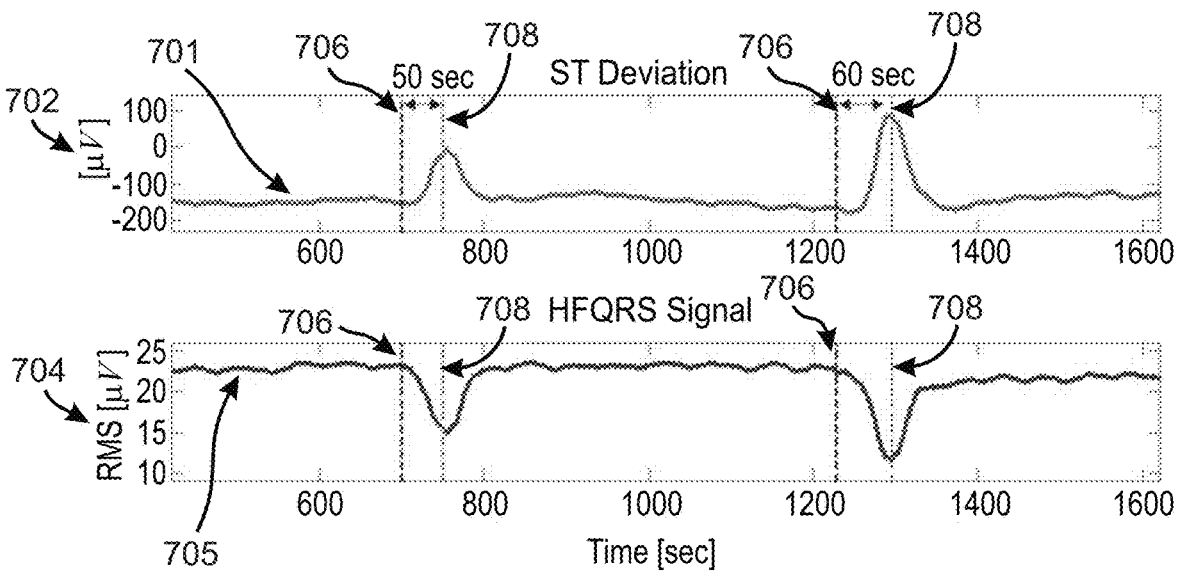
FIGURE 7A
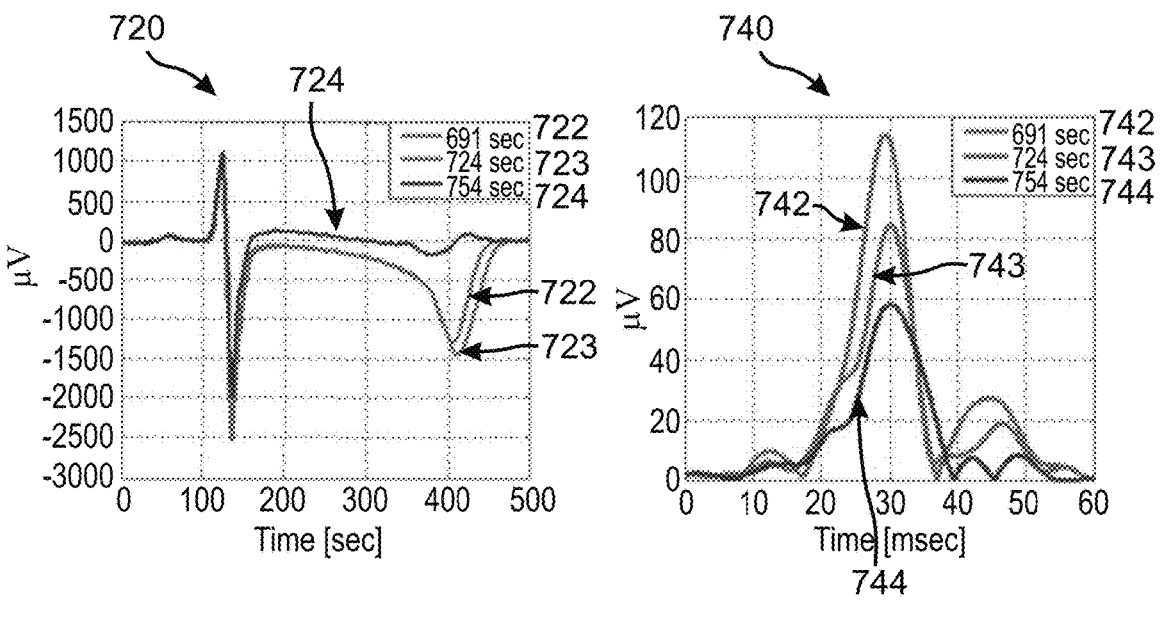
FIGURE 7B                    FIGURE 7C

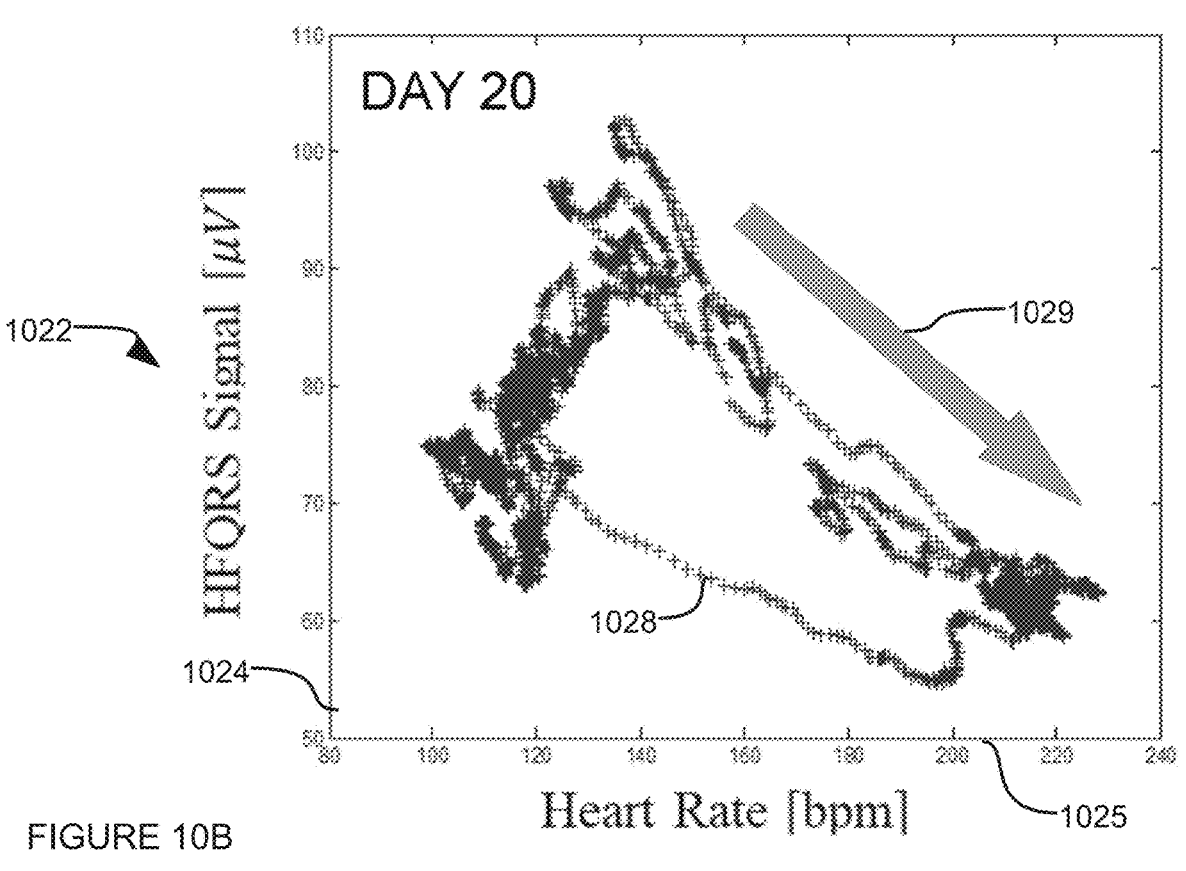
FIGURE 10B
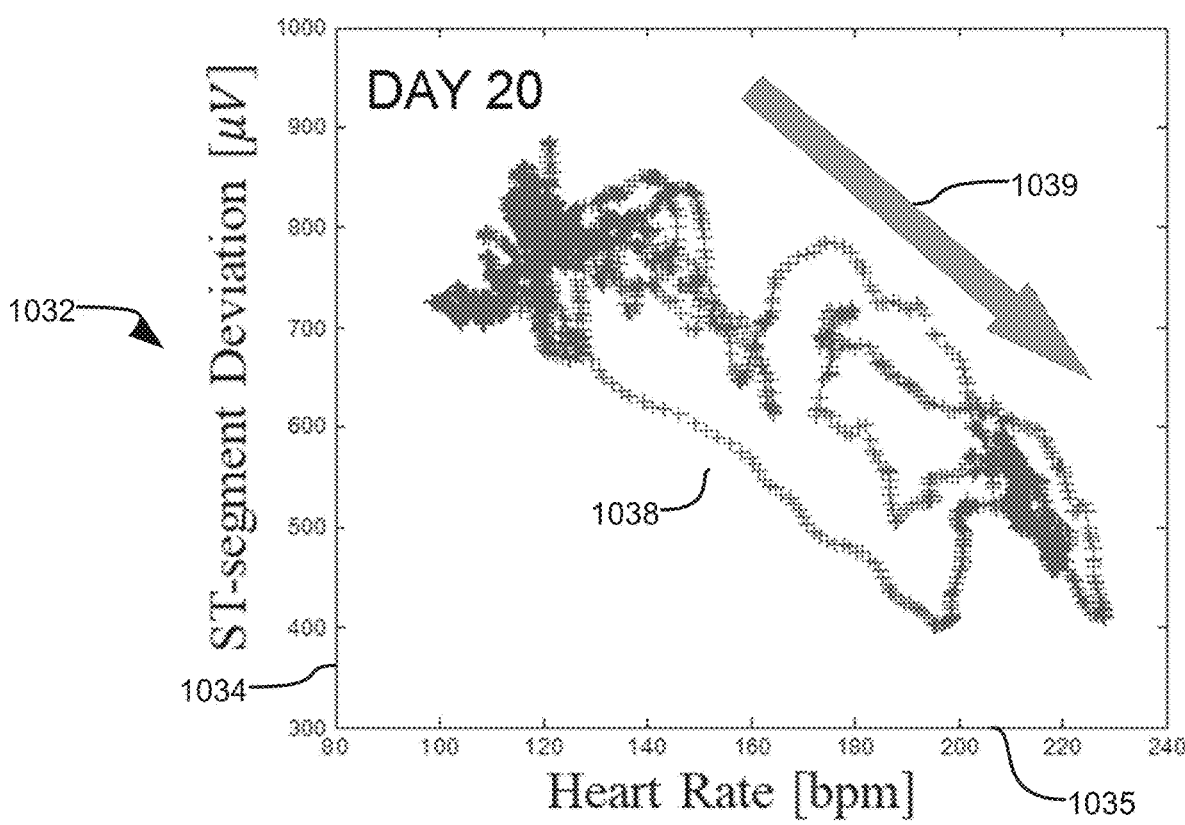

APPARATUS AND METHOD FOR ANALYSIS AND MONITORING OF HIGH FREQUENCY ELECTROGRAMS AND ELECTROCARDIOGRAMS IN VARIOUS PHYSIOLOGICAL CONDITIONS

RELATED APPLICATIONS

This application is a National Phase of PCT Patent Application No. PCT/IL2022/050215 having International filing date of Feb. 24, 2022, which claims the benefit of priority under 35 USC § 119 (e) of U.S. Provisional Patent Application No. 63/152,917 filed on Feb. 24, 2021. The contents of the above applications are all incorporated by reference as if fully set forth herein in their entirety.

FIELD AND BACKGROUND OF THE INVENTION

The present invention, in some embodiments thereof, relates to an apparatus and method for detecting myocardial ischemia using analysis of high frequency components of an electrocardiogram and/or of an electrogram, and, more particularly but not exclusively, to analysis including taking account of physiological conditions such as heart rate and/or breathing rate and/or tidal volume of breathing.

The terms "electrocardiogram" and "ECG" are used throughout the present specification and claims to mean the electrical activity of the heart as sensed using electrodes placed on a subject's skin.

The term "electrogram" is used throughout the present specification and claims to mean the electrical activity of the heart as sensed using electrodes placed within a subject's body.

The electrocardiogram (ECG) and the electrogram are used to measure rate and regularity of heartbeats, as well as the size and position of the chambers, presence of any damage to the heart, and effects of drugs or devices used to regulate the heart.

Usually two or more electrodes are used for ECG measurement, and they can be combined into a number of pairs. The output from each pair is known as a lead.

An ECG is the most common way to measure and diagnose abnormalities in the electrical activity of the cardiac muscle and abnormal rhythms of the heart, particularly abnormalities caused by damage to conductive tissue that carries electrical signals, or abnormal rhythms caused by electrolyte imbalances. In a condition of myocardial infarction (MI), the ECG can identify if the heart muscle has been damaged and sometime also indicate the location of damage, though not all areas of the heart are covered.

An ECG device detects and amplifies tiny electrical changes on a patient's skin that are caused when the heart muscle depolarizes and subsequently repolarizes during each heartbeat. At rest, each cardiac muscle cell is negatively charged (relative to the extracellular charge), causing a negative electric potential across the cardiac muscle cell membrane. The cell's activation phase commences with depolarization, initiated by influx and efflux of positive and negative ions, and decreasing the absolute value of the negative electric potential toward zero. The activation activates mechanical processes in the cardiac muscle cell that cause contraction of the cardiac muscle cell. During each heart cycle, a healthy heart has an orderly progression of a wave of depolarization that is triggered by cells in the sinoatrial node and spreads out through the atrium, then passes through the atrioventricular node and finally spreads all over the ventricles through a unique conduction system which enables multi-site activation. The progression is detected as waveforms in the recorded potential difference (or voltage) between two electrodes placed on either side of the heart and may be displayed as a graph either on a screen or on paper. The produced signal reflects the electrical activity of the heart, and different leads express more clearly different parts of the heart muscle.

A typical ECG tracing of the cardiac cycle (heartbeat) consists of a P wave, a QRS complex, a T wave, and a U wave which is normally visible in 50% to 75% of ECG traces. A baseline voltage of the electrocardiogram is known as the isoelectric line. Typically, the isoelectric line is measured as the portion of the tracing following the T wave and preceding the next P wave.

The standard ECG traces usually filter out high frequency components, in a process named low-pass filtering, typically filtering out frequency components above 100 Hz (e.g. regulatory requirements are usually within a range of 0.05-100 Hz). In some commercial implementations, lower thresholds such as 75 Hz or even 50 Hz are used for the low-pass filtering process. In general, a noise level of the ECG trace is such that high frequency components, above 150 Hz, which are typically measured in micro-volts, cannot be reliably isolated from a single ECG trace and identified or measured. In order to measure and process high frequency components, one typically needs to use signal-to-noise enhancement schemes such as filtering and averaging.

Additional background art includes:

U.S. Pat. No. 8,626,275 to Amit et al, titled "Apparatus and method for detecting myocardial ischemia using analysis of high frequency components of an electrocardiogram";

U.S. Pat. No. 8,538,510 to Toledo et al, titled "Apparatus and method for identifying myocardial ischemia using analysis of high frequency QRS potentials"; and An article by George B. Moody, Roger G. Mark, Andrea Zoccola and Sara Mantero titled "Derivation of Respiratory Signals from Multi-lead ECGs", published in Computers in Cardiology 1985, vol. 12, pp. 113-116, Washington, DC: IEEE Computer Society Press, describes a signal-processing technique which derives respiratory waveforms from ordinary ECGs, permitting detection of respiratory efforts.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to an apparatus and method for detecting myocardial ischemia using analysis of high frequency components of an electrocardiogram and/or of an electrogram, and, more particularly but not exclusively, to analysis including taking account of physiological conditions such as heart rate and/or breathing rate and/or tidal volume.

According to an aspect of some embodiments of the present disclosure there is provided a method of analyzing a subject's cardiac condition, the method including measuring an ECG or an electrogram signal, extracting a high frequency (HF) portion from a QRS portion of the ECG or electrogram signal, producing a HFQRS signal, calculating a HF value based on analyzing the HFQRS signal, measuring at least one more physiological value associated with the subject, and analyzing the ECG or the electrogram signal based on the HF value and the physiological value.

According to some embodiments of the disclosure, the calculating a HF value based on analyzing the HFQRS signal includes calculating a HFQRS signal value.

According to some embodiments of the disclosure, the HF value is recorded for a plurality of different physiological states.

According to some embodiments of the disclosure, the HF value includes a HF signal RMS.

According to some embodiments of the disclosure, the physiological value is a heart rate.

According to some embodiments of the disclosure, the calculating a HF value includes calculating a first HF value and calculating a second HF value, the measuring at least one more physiological value includes measuring a first physiological value associated with a time when the first HF value was measured and measuring a second physiological value associated with a time when the second HF value was measured.

According to some embodiments of the disclosure, the analyzing includes producing a scatter plot of a plurality of points, each point defined by a pair of a first value of the HF value and a second value of the physiological value.

According to some embodiments of the disclosure, the analyzing includes calculating a slope of a regression line passing through the plurality of points in the scatter plot.

According to some embodiments of the disclosure, the analyzing includes determining a likelihood of ischemia based on the slope.

According to some embodiments of the disclosure, the analyzing includes producing a determination that ischemia is likely based on a non-positive value of the slope.

According to some embodiments of the disclosure, the analyzing by the plurality of points includes points captured at a plurality of different heart rates.

According to some embodiments of the disclosure, the analyzing includes calculating a calculated value based on the HF value and the physiological value.

According to some embodiments of the disclosure, the calculated value is a ratio of a current measured HFQRS signal RMS over a period of time, and a resting HFQRS signal RMS, measured in resting condition, and the physiological value is a ratio of a current measured HR over the period of time, and a resting HR, measured in resting condition.

According to some embodiments of the disclosure, the calculated value is equal to:

$$\frac{NHFRMS}{NHR} = \frac{(\max(HF) - \min(HF))}{((\text{current}_{HR}) - (\text{resting}_{HR}))}$$

wherein

NHFRMS is a difference between a maximum current measured HFQRS signal RMS over the period of time, and a minimum HFQRS signal RMS, measured in resting condition, NHR is a difference between the current measured HR over the period of time, and the resting HR, measured in resting condition, Max(HF) is a maximal HF value measured during the time period, Min(HF) is a minimal HF value measured during the time period, currentHR is a measurement of average HR over the period of time, and restingHR is an average HR measured in resting condition.

According to some embodiments of the disclosure, the physiological value is a normalized heart rate (NHR), wherein the NHR is a ratio of a measured HR over a first period of time, and a resting HR, measured in resting condition, over a second period of time.

According to some embodiments of the disclosure, the calculated value includes a value based on dividing a first value of a measurement of the HF value by a second value of the HF value at rest.

According to some embodiments of the disclosure, the restingHR value is retrieved from storage, for the subject.

According to some embodiments of the disclosure, the restingHR value is retrieved from storage, for a category of subjects to which the subject is associated.

According to some embodiments of the disclosure, the physiological value is a measured breathing rate.

According to some embodiments of the disclosure, the physiological value is a value associated with a depth of breathing.

According to some embodiments of the disclosure, the physiological value is a tidal volume of breathing.

According to some embodiments of the disclosure, the physiological value is a measured breathing rate measured by analyzing the ECG or electrogram signal.

According to some embodiments of the disclosure, the breathing rate is calculated based on measuring intervals between R waves in consecutive QRS complexes.

According to some embodiments of the disclosure, the HFQRS signal value includes a value based on measuring a Reduced Amplitude Zone (RAZ) in the HFQRS signal.

According to some embodiments of the disclosure, the HFQRS signal value includes a ratio of a length of an interval between two adjacent local maxima of an envelope of the HFQRS signal and a length of the QRS complex.

According to some embodiments of the disclosure, the HFQRS signal value includes a ratio of an area of a basin of the RAZ to an area of the HFQRS signal envelope.

According to some embodiments of the disclosure, the HFQRS signal value is a ratio of a measured HFQRS signal value over a first period of time, and a resting HFQRS signal value, measured in resting condition, over a second period of time, and the physiological value is a ratio of a measured HR over the first period of time, and a resting HR, measured in resting condition, over the second period of time.

According to an aspect of some embodiments of the present disclosure there is provided a system for analyzing an electro-cardiogram (ECG) or electrogram signal, the apparatus including an input for an ECG or electrogram signal, a high frequency (HF) signal extractor which extracts a HF portion from the ECG or electrogram signal, and a processor configured to calculate a HF (HF components of the ECG or electrogram signal) value based on analyzing the HF portion, measure at least one more physiological value associated with a subject, and analyze the ECG or the electrogram signal based on the HF value and the physiological value.

According to some embodiments of the disclosure, the HF value includes a HFQRS signal value based on analyzing HF components of a QRS complex in the ECG or electrogram signal.

According to some embodiments of the disclosure, the physiological value is a heart rate.

According to some embodiments of the disclosure, the processor is configured to produce a scatter plot of a plurality of points, each point defined by a pair of a first value of the HF value and a second value of the heart rate.

According to some embodiments of the disclosure, the system is configured to display the scatter plot.

According to some embodiments of the disclosure, the processor is configured to calculate a slope of a regression line passing through the plurality of points in the scatter plot.

According to some embodiments of the disclosure, the processor is configured to produce a scatter plot based on the plurality of points including points captured at a plurality of different heart rates.

According to some embodiments of the disclosure, the system is configured for saving the HF value and the physiological value.

According to some embodiments of the disclosure, the processor is configured to calculate a calculated value based on the HF value and the physiological value.

According to some embodiments of the disclosure, further including the apparatus configured for saving the calculated value.

According to an aspect of some embodiments of the present disclosure there is provided a method of performing a cardiac stress test, the method including starting a cardiac stress test, measuring an ECG or an electrogram signal, extracting a high frequency (HF) portion from the ECG or electrogram signal, producing a HFQRS signal, calculating a plurality of HF values at a plurality of different times based on analyzing the HFQRS signal at the plurality of different times, measuring a plurality of corresponding values of at least one more physiological parameter at a same plurality of times as the plurality of HF values, and stopping the cardiac stress test based on at least some of the plurality of physiological parameter values being different from each other.

According to some embodiments of the disclosure, the stopping the cardiac stress test includes stopping the cardiac stress test based on at least some of the plurality of physiological parameter values being sufficiently different from each other.

According to some embodiments of the disclosure, the physiological parameter includes heart rate, and the stopping the cardiac stress test includes stopping the cardiac stress test before the heart rate reaches a target heart rate of a Bruce test.

According to some embodiments of the disclosure, the physiological parameter includes heart rate, and the stopping the cardiac stress test includes stopping the cardiac stress test before the heart rate reaches a target heart rate of a six-minute test.

According to some embodiments of the disclosure, further including analyzing the ECG or the electrogram signal based on the plurality of HF values and corresponding plurality of physiological values.

According to an aspect of some embodiments of the present disclosure there is provided a method of analyzing a subject's cardiac condition, the method including measuring an ECG or an electrogram signal, extracting a high frequency (HF) portion from the ECG or electrogram signal, producing a HFQRS signal, calculating a plurality of HF values at a plurality of different times based on analyzing the HFQRS signal at the plurality of different times, measuring a plurality of corresponding values of at least one more physiological parameter at a same plurality of times as the plurality of HF values, and analyzing the ECG or the electrogram signal based on the plurality of HF values and corresponding plurality of physiological values.

According to some embodiments of the disclosure, the analyzing includes analyzing based on at least some of the plurality of physiological parameter values being sufficiently different from each other.

According to some embodiments of the disclosure, the physiological parameter includes heart rate, and the analyzing includes analyzing before the heart rate reaches a target heart rate of a Bruce test.

According to some embodiments of the disclosure, the physiological parameter includes heart rate, and the analyzing includes analyzing before the heart rate reaches a target heart rate of a six-minute test.

According to some embodiments of the disclosure, further including analyzing the ECG or the electrogram signal based on the plurality of HF values and corresponding plurality of physiological values.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present disclosure may be embodied as a system, method or computer program product. Accordingly, some embodiments of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of the method and/or system of the disclosure, several selected tasks could be implemented by hardware, by software or by firmware and/or by a combination thereof, e.g., using an operating system.

For example, hardware for performing selected tasks according to some embodiments of the disclosure could be implemented as a chip or a circuit. As software, selected tasks according to some embodiments of the disclosure could be implemented as a plurality of software instructions being executed by a computer using any suitable operating system. In an exemplary embodiment of the disclosure, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as analyzing a high-frequency ECG, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings:

FIG. 4C is a simplified flow chart illustration of a method of analyzing a subject's cardiac condition according to an example embodiment of the invention;

FIG. 7A shows two graphs of significant response, of both ST and iHFQRS signals according to an example embodiment;

FIGS. 7B and 7C show two graphs depicting if an electrogram and a HFQRS envelope during occlusion according to an example embodiment;

FIGS. 10A-10C are graphs according to an example embodiment showing ST and HFQRS signal values collected during an induced ischemia episode.

DESCRIPTION OF SPECIFIC EMBODIMENTS OF THE INVENTION

Figure 1A:
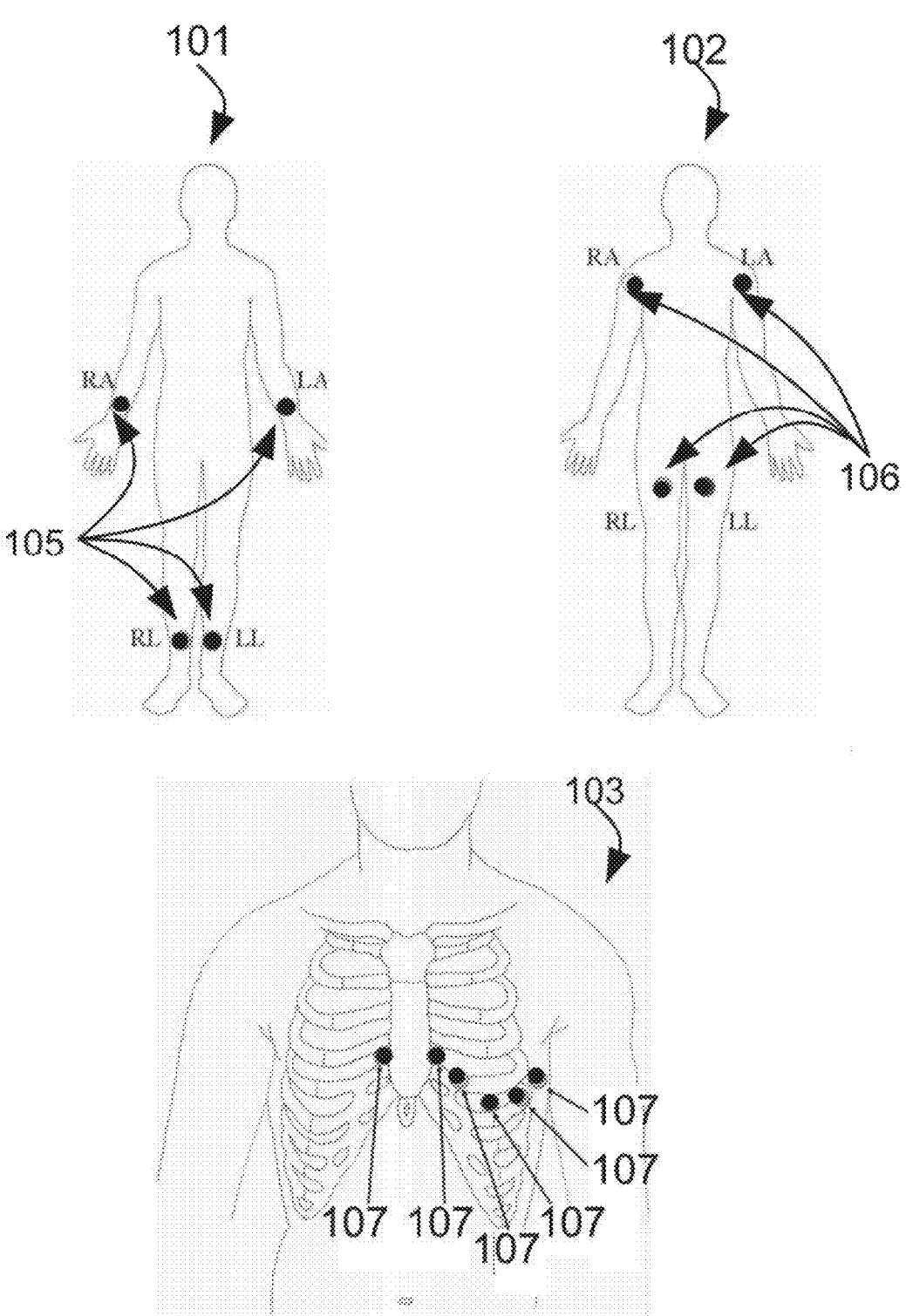
FIG. 1A is a simplified illustration of typical prior art locations for attaching pickup electrodes, including electrodes for picking up high frequency components of an electrogram.

The present invention, in some embodiments thereof, relates to an apparatus and method for detecting myocardial ischemia using analysis of high frequency components of an electrocardiogram and/or of an electrogram, and, more particularly but not exclusively, to analysis including taking account of physiological conditions such as heart rate and/or breathing rate.

Overview

Various methods and device have been described for analyzing high frequency (HF) ECG signals, for example in above-mentioned U.S. Pat. No. 8,626,275 to Amit et al and U.S. Pat. No. 8,538,510 to Toledo et al, optionally producing various parameters describing the HF ECG signals, and optionally detecting potential ischemia and/or additional cardiac conditions based on values of the parameters. A non-limiting example parameter includes a measurement of a Reduced Amplitude Zone (RAZ) in a contour of an envelope of the HF ECG.

An aspect of some embodiments includes methods and devices for analyzing HF ECG or electrogram signals measured under different heart rate conditions.

In some embodiments, a change between HF ECG electrogram signals measured under different heart rate conditions potentially indicates likelihood of ischemia.

In some embodiments, a value of a change between HF ECG electrogram signals measured under different heart rate conditions potentially indicates likelihood of ischemia, when the change is greater than a threshold value.

In some embodiments, two HFQRS signal values taken at two different heart rates are compared, and if the HFQRS signal value sampled at the higher heart rate is not higher than the HFQRS signal value sampled at the lower heart rate, a likelihood of ischemia is optionally indicated.

In some embodiments, a subject optionally starts a stress test, optionally a standard stress test such as a Bruce test or a 6-minute test, and even though the stress test ends earlier than expected, for whatever reason, analysis of HF ECG or electrogram measurements taken at different heart rates, potentially produces an indication of ischemia. By way of a non-limiting example, a subject does not reach the subject's target heart rate, and an indication of likelihood of ischemia may optionally be produced based on analysis of HF ECG or electrogram measurements taken at different heart rates.

In some embodiments, a subject has a device collecting HF ECG or electrogram measurements collecting his/her HF ECG or electrogram measurements over a period of time, not necessarily during a stress test. The device may be, by way of some non-limiting examples, an ICD (Implantable Cardiac Device) or a CRT (Cardiac Resynchronization Therapy) device or a holter. In some embodiments, the device optionally records HF ECG or electrogram measurements and heart rate. Analysis of the HF ECG or electrogram measurements at different heart rate values optionally provides an indication of ischemia. In some embodiments, the device optionally records HF ECG or electrogram measurements and breathing rate. Analysis of the HF ECG or electrogram measurements at different breathing rate values optionally provides an indication of ischemia.

In some embodiments, a scatter plot of HFQRS signal values VS heart rate values is produced and optionally displayed. In some embodiments, analysis of the scatter plot optionally causes a physician to indicate a likelihood of ischemia.

In some embodiments, a same system which measures HFQRS signal values and heart rate values stores pairs of HFQRS signal values and heart rate values sampled at a same time.

In some embodiments, the system optionally produces a scatter plot as described above based on the stored values. In some embodiments, the system optionally calculates a regression line using the pair of values. In some embodiments, the system optionally produces an indication of potential ischemia based on one or more parameters of the regression line. In some embodiments, the system optionally produces an indication of potential ischemia based on a value of a slope of the regression line. In some embodiments, the system optionally produces an indication of potential ischemia based on a positive value of the slope of the regression line.

In some embodiments, the system optionally records a slope of the scatter plot for a particular period of time, and optionally continues monitoring the slope over additional time. In some embodiments, if the slope gradually changes over time, the system optionally produces an indication that the slope is changing. In some embodiments, if the slope gradually decrease over time, and/or the value of the slope becomes more negative over time, the system optionally produces an indication of likelihood of ischemia.

An aspect of some embodiments includes methods and devices for analyzing HF ECG or electrogram signals measured under different physiological conditions, optionally producing various parameters describing the HF ECG or electrogram signals, and optionally detecting potential ischemia and/or additional cardiac conditions based on the analysis of values of the parameters as relating to measures of the physiological condition.

A non-limiting example HF ECG or electrogram parameter includes a measurement of a Reduced Amplitude Zone (RAZ) in a contour of an envelope of the HF ECG or electrogram. In some embodiments, a first value of the parameter is construed to indicate potential ischemia when a physiological parameter, such as heart rate or breathing rate, is low, and a second value of the HF ECG or electrogram parameter is construed to indicate potential ischemia when the physiological parameter value is high.

In some embodiments, a table relating values of one or more physiological parameters to values of one or more HF signal analysis parameters to potential cardiac conditions, is used to detect and/or indicate potential of a patient having such a cardiac condition. In some embodiments, a look-up-table (LUT) relating values of one or more physiological conditions to values of one or more HF signal analysis parameters to potential cardiac conditions, is used to detect and/or indicate potential of a patient having such a cardiac condition.

In some embodiments, a machine learning technique such as a neural net is optionally used to detect and/or indicate potential of a patient having such a cardiac condition, based on training with values of HF signal analysis parameters and values of physiological parameters.

Some non-limiting examples of HF signal parameters include:

HFRMS—square root of the mean square (or quadratic mean) of the high frequency component of the ECG signal;

RAZ area—a RAZ is a pattern of a notch or gap in an envelope of amplitude of the HF ECG or electrogram signal. The RAZ area is a duration of the RAZ in the time domain; and RAZ ratio or RAZ percent—a ratio of, or a percentage of, an area of basin(s) (depressions in the upper contour of the envelope) relative to an area under the upper contour of the envelope.

Some non-limiting examples of physiological parameters include:

heart rate;

breathing rate;

normalized breathing rate, defined as a difference between a current measured breathing rate over a current period of time, and a resting breathing rate, measured over a period of time in a resting condition tidal volume—a volume representing a normal volume of air displaced between normal inhalation and exhalation when no extra effort is applied; and blood pressure.

It is noted that the physiological parameters may optionally be obtained by the same sensors and processors as used for obtaining the HF signal parameters. For example, heart rate can be obtained from an ECG signal, as is known in the art. For example, breathing rate can be obtained from an ECG signal, as described, by way of a non-limiting example, in above-mentioned article titled "Derivation of Respiratory Signals from Multi-lead ECGs" by Moody et al.

Figure 1B:
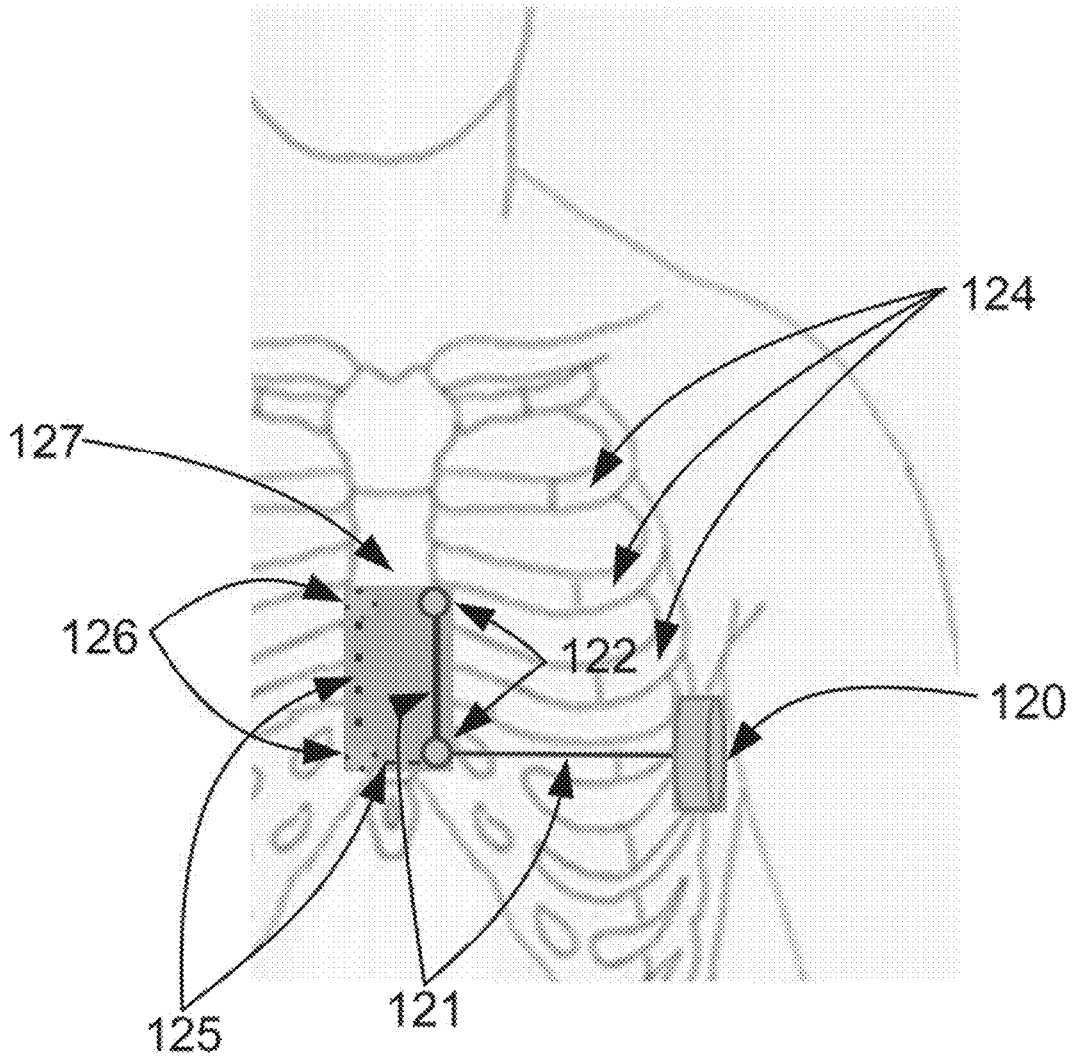
FIG. 1B is a simplified illustration of a prior art subcutaneous apparatus for analyzing an electrogram.
Figure 2:
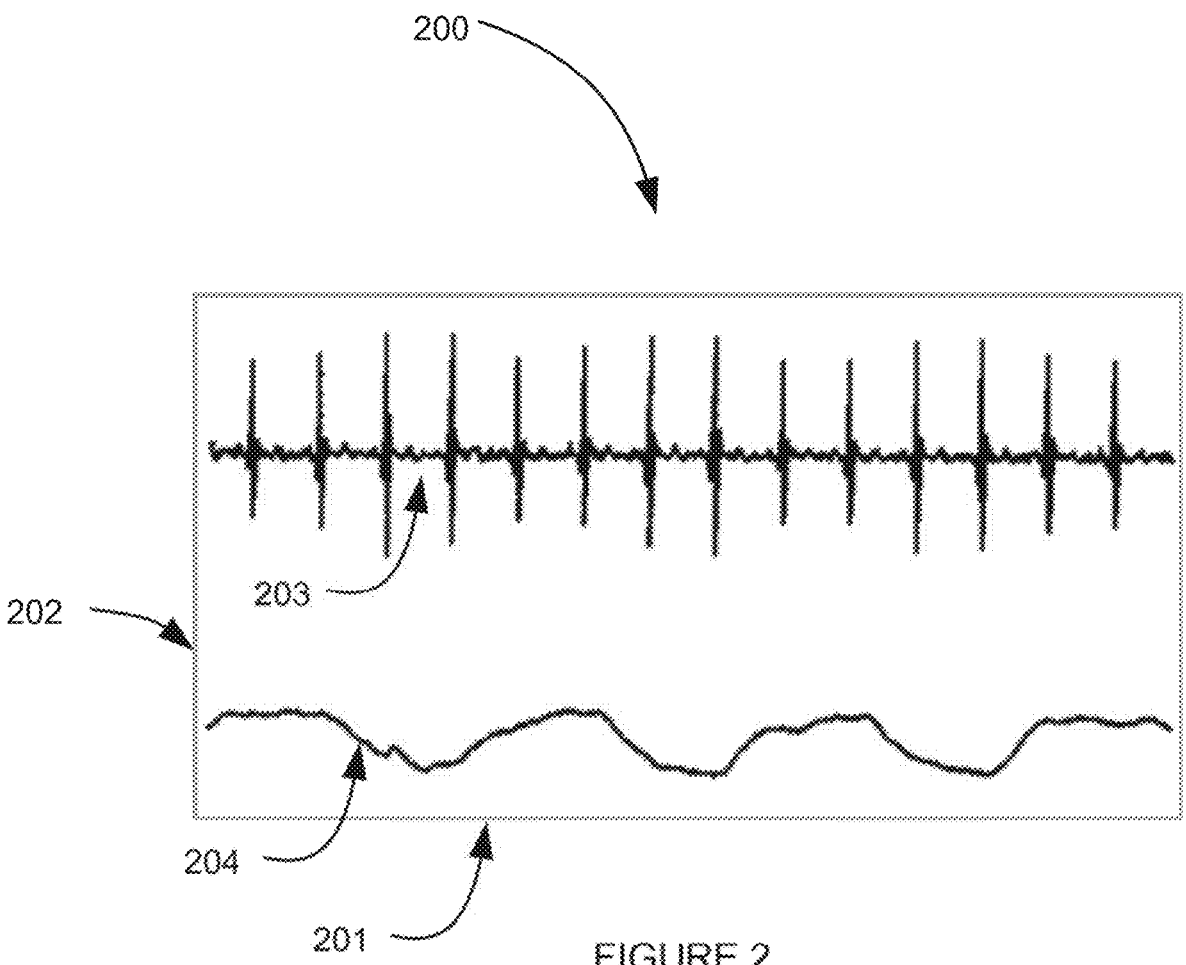
FIG. 2 is a simplified illustration of a prior art method for determining breathing rate based on analyzing an electrogram.

For purposes of better understanding some embodiments of the present disclosure, reference is first made to the measurement of an electrocardiogram and electrogram as illustrated in FIGS. 1A and 1B, and of measurement of breathing rate based on an ECG signal as illustrated in FIG. 2.

Reference is now made to FIG. 1A, which is a simplified illustration of typical prior art locations for attaching pickup electrodes, including electrodes for picking up high frequency components of an electrogram.

FIG. 1A depicts three line FIGS. 101 102 103 of human subjects, and three sets of locations 105 106 107 for placing electrodes for picking up high frequency components of an electrocardiogram.

Reference is now made to FIG. 1B, which is a simplified illustration of a prior art subcutaneous apparatus for analyzing an electrogram.

FIG. 1B depicts a simplified illustration of a subcutaneously implanted electronics box, also termed a can 120, and with one or more electrode wires 121 125 optionally electrically connecting the can 120 with one or more electrodes at one or more subcutaneous electrogram signal pickup locations 122 126.

In some embodiments, the can 120 is electrically connected by the electrode wires 121 to example electrodes at subcutaneous pickup locations 122 depicted in FIG. 1B, which are optionally over the ribs 124, under the skin (not shown) and on a left edge of a subject's sternum 127.

In some embodiments, the can 120 is electrically connected by electrode wires 125 to electrodes at example pickup locations 126 depicted in FIG. 1B, which are optionally over the ribs 124, under the skin (not shown) and on a right edge of the subject's sternum 127.

It is noted that implanted pickup locations 122 126, even external to the ribs 124, potentially benefit from a signal which contains significantly less noise than a pickup location on the skin surface.

Reference is now made to FIG. 2, which is a simplified illustration of a prior art method for determining breathing rate based on analyzing an electrocardiogram.

FIG. 2 shows a graph 200 of respiration-induced modulation of QRS complex amplitude in a regular ECG signal. The graph 200 has an X-axis 201 showing time, and a Y-axis 202 showing signal amplitude. An upper trace 202 shows an ECG trace, and a lower trace 204 shows respiration as measured by a pneumatic respiration transducer (PRT) placed around a chest of a subject. The upper trace 202 and the lower trace 204 show measurements over a duration of 10 seconds. The graph 200 is taken from the above-mentioned article titled "Derivation of Respiratory Signals from Multi-lead ECGs" by Moody et al.

FIG. 2 depicts and the article teaches a method for analyzing QRS complex amplitude in a regular ECG signal and respiratory actions.

Now with reference to example embodiments, and by way of a non-limiting example, the amplitude of the QRS complex is seen to increase and decrease in relation to the respiration.

In some embodiments stages of the breathing are optionally measured by one or more motion sensors in or connected to a patient. In some embodiments the stages of the breathing are optionally measured by a strap around the chest.

In some embodiments the stages of the breathing are optionally measured by an audio sensor. Such detection by audio sensors can potentially operate both in implantable devices and in external devices.

In some embodiments the stages of the breathing are optionally measured by a spirometric device. A spirometric device may be in a unit external to a subject's body. In some embodiments, a spirometric unit may send a signal to an implanted unit to enable detecting the stages of the breathing.

In some embodiments, detecting a portion of the breathing cycle is optionally performed by using motion sensors and analysis to detect cyclic movement of a subject's chest.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

An aspect of some embodiments relates to quantification of high frequency signals of an electrocardiogram within the setting of an externally attached monitor device such as an ECG device, a holter (a type of ambulatory electrocardiography device), a wearable ECG device (ECG system that is carried on the patient's body during regular daily activity), an "ECG watch" (wrist-band ECG device) etc., and an electrogram within the setting of an implantable device, subcutaneous electrodes, intra-cardiac electrodes or intracoronary electrodes. In some embodiments, the device measuring the electrocardiogram or the electrogram is optionally a recording device. In some embodiments, the device measuring the electrocardiogram or the electrogram is optionally a continuous measurement and/or continuous recording device.

In some embodiments, the implantable device can be an independent sensing and analysis device or in conjunction with another implantable device such as a pacemaker, ICD (Implantable Cardiac Device) or CRT (Cardiac Resynchronization Therapy) device. An implanted device may use implantable electrodes for sensing the electrogram. Such electrodes may be located on the device itself, or placed in a proximity of a heart in intra-cardiac or/and endocardial and/or intracoronary locations. The electrodes can measure an electrogram signal between 2 electrodes, between 2 electrode tips (i.e. distal and proximal tips) or between an electrode and the device's can (the box or package containing the implantable device).

In some embodiments, high frequency (HF) analysis of a QRS segment of the electrogram or electrocardiogram is used for detecting myocardial ischemia. In some embodiments, the high frequency analysis can produce one or more parameters based on the analysis of a high frequency electrocardiogram (ECG) or electrogram (EGM) signal of the QRS segment, both of which will be referred below as a HFQRS Signal. The term "HFQRS signal" is used throughout the present specification and claims for a high frequency portion of the electrocardiogram (ECG) or electrogram (EGM) signal of the QRS segment.

Some non-limiting example parameters are listed below:

A Root Mean Square (RMS) of the HFQRS signal (HFRMS). The RMS of a HFQRS Signal typically decreases during ischemia; and Existence and quantification of Reduced Amplitude Zones (RAZ) in a HFQRS Signal.

A High Frequency QRS (HFQRS) signal includes high-frequency components of the QRS complex portion of an ECG or an electrogram. The HFQRS signal is typically a small signal, typically measured in microvolts. The HFQRS signal provides information about the depolarization phase of the cardiac cycle, and has shown a superior accuracy in detection of stress induced ischemia compared to changes in the repolarization phase. In some embodiments, the HFQRS signal is typically measured and/or analyzed in a frequency band of 150-250 Hz, or even a frequency band of 150-500 Hz.

HFRMS—is a term used for the square root of the mean square (or quadratic mean) of the high frequency of the QRS complex, that is, the high frequency component of a QRS complex.

HFQRS Envelope—is a term used for the time-domain envelope of the HFQRS complex. In some embodiments, the HFQRS envelope is determined for each lead. In some embodiments, the HFQRS envelope may be calculated using a Hilbert transform followed by a low-pass filter, as described in above mentioned U.S. Pat. No. 8,626,275.

Reduced Amplitude Zone (RAZ)—is a term used to refer to patterns of notches or gaps in the amplitude of the envelope of the HFQRS signal (in the time-domain). A RAZ is defined as an interval between two adjacent local maxima of an upper contour of the envelope. In some embodiments, a local maximum has an absolute value higher than, by way of a non-limiting example, three preceding and three following envelope points.

In some embodiments, a non-limiting RAZ quantification technique includes calculating a percentage of an area of basins (depressions in the upper contour of the envelope, or depressions in the higher peak of the envelope) relative to an area under the upper contour of the envelope.

In some embodiments, a decrease in RMS and the quantification of RAZ may be adjusted to the absolute heart rate (HR) or to a Normalized heart rate (NHR).

The NHR is optionally calculated as a ratio of a current HR and an average resting HR, optionally measured over a period of time in resting condition.

In some embodiments, the adjustment is optionally made by dividing a fraction denoting a decrease in RMS value or the RAZ value, by the HR or by the NHR. In some embodiments, instead of a division function, another function may be used to achieve adjustment of RMS or RAZ parameters high various values of HR.

The HFQRS is measured in various configurations enabling analysis of electrical activity in multiple vectors according to the location of the leads relative to the device's can and between pairs of leads or combinations of the leads.

The high frequency signal used, for example, for detecting myocardial ischemia is relatively low in amplitude compared to noise, even for intra-cardiac signals. In some embodiments, it may be preferable to align and average several QRS intervals, optionally QRS intervals which are close in time and therefore may be assumed to be part of a relatively non-changing physiological condition of a patient. Such an averaging procedure potentially increase the Signal-to-Noise-Ration (SNR), potentially allowing for a more accurate analysis. In the above-described case the "close in time" optionally means within 10, 20, 30, up to 180 seconds. In some embodiments, the term "close in time" optionally means over a time period when the heart rate changes by no more than X percent, for example by no more than 5%, 10%, 15%.

In some embodiments, a linkage between the breathing cycle and the heart rate is known in the literature and referred to as Respiratory Arrhythmia.

In some embodiments, the heart rate is among the factors that govern the behavior of the HFQRS signal, which results in a coupling between HFQRS parameters and the breathing cycle. In some embodiments, it is potentially beneficial to track the breathing cycle and compare the HFQRS results between measurements taken at similar locations of the breathing cycle, for example, at maximum exhalation.

In some embodiments, in order to potentially improve power consumption, it the HFQRS signal is measured only once during a breathing cycle, optionally at a same portion of the breathing cycle, instead of at every heartbeat.

Using state-of-the-art sensors it is potentially possible to measure blood pressure in various loci, for example, in the pulmonary arteries. Such measurements potentially provide a more accurate description of the patient's physiological status and potentially correlate to HFQRS parameters, as well as other parameters of a given physiological conditions. The HFQRS parameter may have natural variations under normal circumstances. Gating or triggering the analysis of the signal based on values of physiological parameters such as blood pressure, pulse and breathing cycle, may render the HFQRS more sensitive and accurate, potentially increasing its usefulness for the indication of ischemic states and ischemic disease.

In some embodiments, the simultaneous acquisition, registration and analysis of HFQRS and such additional physiological parameters (blood pressure, pulse, etc.) potentially have two consequences. First, the HFQRS can be analyzed and evaluated with respect to a multi-parameter state when recording a person's baseline. Second, it is possible to make HFQRS measurements or analysis only at certain, possibly predetermined, multi-parameter states.

In some embodiments, determining a baseline for comparison in order to detect, by way of a non-limiting example, ischemia, is optionally done by continuous measurements and constant updating. Acute ischemia is potentially detected, either by reaching specific HFQRS values or Normalized HFQRS values, or by specific changes compared to baseline. By tracking the parameters of the baseline itself it is also possible to detect a gradual deterioration in the patient's condition.

Figure 3A:
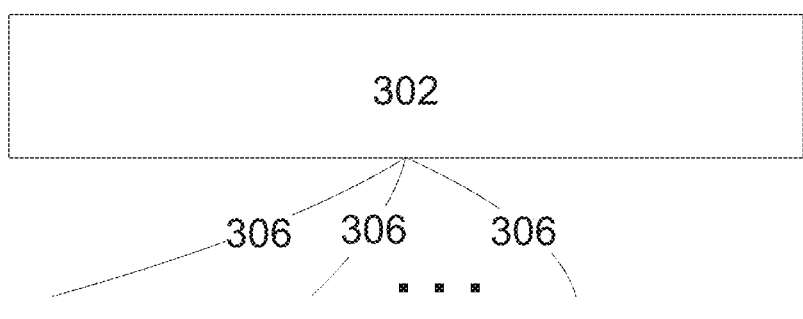
FIG. 3A is a simplified illustration of apparatus for detecting myocardial ischemia using analysis of high frequency components of an electrogram and/or electrocardiogram according to an example embodiment of the invention.

Reference is now made to FIG. 3A, which is a simplified illustration of apparatus for detecting myocardial ischemia using analysis of high frequency components of an electrogram and/or electrocardiogram according to an example embodiment of the invention.

FIG. 3A shows a schematic depiction of an HF electrogram and/or electrocardiogram analyzer 302, and one or more electrodes 306 for collecting electrogram signals.

In some embodiments, the analyzer 302 may be included in an implantable device.

In some embodiments, one or more of the electrodes may be attached to a body of the device, also termed a can of the device.

In some embodiments, the analyzer 302 is optionally connected to one or more of the same electrodes as used by a pacemaker and/or ICD and/or CRT.

In some embodiments, the analyzer 302 may optionally be included in a same body or can as a pacemaker and/or ICD and/or CRT.

In some embodiments, the electrodes 306 may include one or more of electrodes for placing on a skin, endo-cardiac electrodes, intra-cardiac electrodes and/or intracoronary electrodes.

In some embodiments, monopolar electrodes and/or bipolar electrodes and/or multipolar electrodes or a mix thereof are used.

Figure 3B:
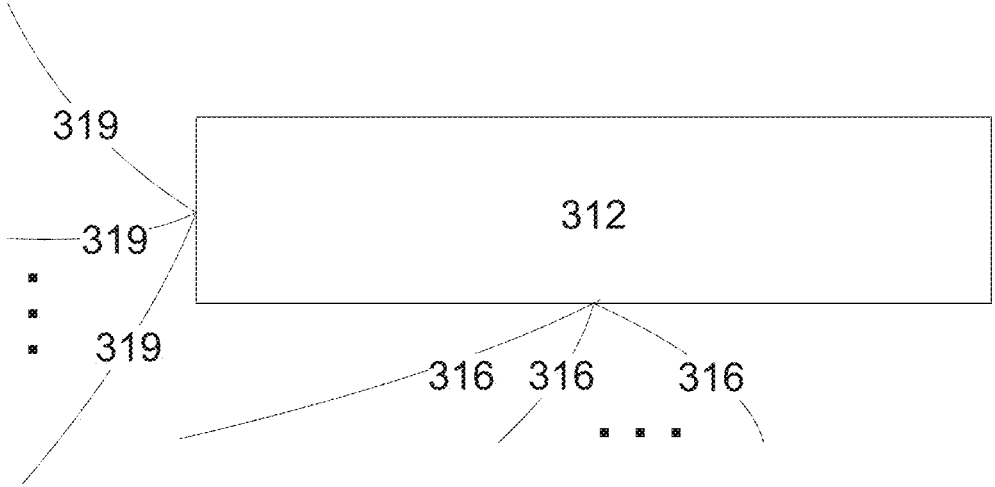
FIG. 3B is a simplified illustration of apparatus for detecting myocardial ischemia using analysis of high frequency components of an electrogram and/or electrocardiogram according to an example embodiment of the invention.

Reference is now made to FIG. 3B, which is a simplified illustration of apparatus for detecting myocardial ischemia using analysis of high frequency components of an electrogram and/or electrocardiogram according to an example embodiment of the invention.

FIG. 3B shows a schematic depiction of an HF electrogram and/or electrocardiogram analyzer 312, one or more ECG and/or electrocardiogram electrodes 316 for collecting electrogram and/or electrocardiogram signals, and one or more electrodes 319 for collecting physiological signals other than ECG and/or electrocardiogram.

In some embodiments, the analyzer 312 may be included in an implantable device.

In some embodiments, one or more of the electrodes 316 319 may be attached to a body of the device, also termed a can of the device.

In some embodiments, the analyzer 312 is optionally connected to one or more of the same electrodes 316 319 as used by a pacemaker and/or ICD and/or CRT.

In some embodiments, the analyzer 312 may optionally be included in a same body or can as a pacemaker and/or ICD and/or CRT.

In some embodiments, the electrodes 316 319 may include one or more of electrodes for placing on a skin, endo-cardiac electrodes, intra-cardiac electrodes and/or intracoronary electrodes.

In some embodiments, monopolar electrodes and/or bipolar electrodes and/or multipolar electrodes or a mix thereof are used.

In some embodiments, the one or more electrodes 319 for collecting physiological signals other than ECG and/or electrocardiogram are optionally used to estimate blood pressure (for example using data from a PPG (photoplethysmogram), and/or breathing rate (for example using one or more piezoelectric transducer(s) and/or one or more accelerometer(s) and/or an intranasal pressure transducer).

In some embodiments, detection of ischemia onset and/or monitoring of an ischemic condition is optionally based on measuring a change in one or more parameters of a high frequency signal of a single and/or multiple leads of ECG (Electrocardiogram) or Electrogram using one or more external electrodes or one or more intra-cardiac electrode.

Some non-limiting examples of parameters of the high frequency signal include:

An HR-adjusted decrease in HFQRS signal RMS, adjustment optionally being achieved by dividing the fraction denoting the decrease in RMS by a value of an absolute heart rate (HR).

A NHR-adjusted decrease in RMS, adjustment optionally being achieved by dividing the fraction denoting a decrease in RMS by a Normalized HR (NHR). One non-limiting example for calculating the NHR is calculating a ratio of a current HR, measured over a first period of time, typically 10 seconds, or in a range of 5, 10, 20, 30, 40, 50 and 60 seconds, and an average resting HR, measured over a second, same or different, period of time, typically 60 seconds, in resting condition. This can be described mathematically as follows (where HF is the high frequency signal):

$$\frac{HFRMS_{Decrease}}{NHR} = \frac{(\max(HF) - \min(HF))}{((\text{Current}_{HR}) - (\text{resting } HR))}$$

A HR-adjusted decrease in RAZ measure, adjustment optionally being achieved by dividing a RAZ measure by an absolute heart rate (HR).

A NHR-adjusted decrease in RAZ measure, adjustment optionally being achieved by dividing a RAZ measure by a Normalized HR (NHR). One non-limiting example for calculating the NHR is to calculate the ratio of the current HR, measured over a period of typically 5 seconds, and the average resting HR, measured over a period of time, typically 60 seconds, in resting condition.

A HR-adjusted decrease in RMS, adjustment optionally being achieved using a function of the HR and the decrease in RMS, so that HR-adjusted decrease in RMS yields similar values for low RMS decrease during low HR and for high RMS decrease during high HR. A typical, non-limiting example for such a function would be RMSD/exp(HR), where RMSD is the decrease in RMS.

A NHR-adjusted decrease in RMS, adjustment optionally being achieved using a function of the NHR and the decrease in RMS, so that NHR-adjusted decrease in RMS yields similar values for low RMS decrease during low NHR and for high RMS decrease during high NHR. A typical, non-limiting example for such a function would be RMSD/exp(NHR), whereas RMSD is the decrease in RMS. The NHR is optionally calculated as the ratio of the current HR, measured over a period of typically 5 seconds, and the average resting HR, measured over a period of time, typically 60 seconds, in resting condition.

A HR-adjusted decrease in RAZ measure, adjustment optionally being achieved using a function of the HR and the decrease in RAZ, so that HR-adjusted decrease in RAZ yields similar values for low RAZ decrease during low HR and for high RAZ decrease during high HR. A typical, non-limiting example for such a function would be RAZD/exp(HR), whereas RAZD is the decrease in RAZ.

A NHR-adjusted decrease in RAZ measure, adjustment optionally being achieved using a function of the NHR and the decrease in RAZ, so that NHR-adjusted decrease in RAZ yields similar values for low RAZ decrease during low NHR and for high RAZ decrease during high NHR. A typical, non-limiting example for such a function would be RAZD/exp(NHR), where RAZD is the decrease in RAZ. The NHR is optionally calculated as the ratio of the current HR, measured over a period of typically 5 seconds, and the average resting HR, measured over a period of time, typically 60 seconds, in resting condition.

In some embodiments, detection of ischemia onset and/or monitoring of an ischemic condition is optionally based on measuring a change in one or more parameters of a high frequency signal as described above, and also detecting different stages of a breathing cycle. In some embodiments, the stages of the breathing cycle can optionally be characterized by:

a. Amplitude of the QRS complex (in some embodiments, specifically amplitude of R-waves)

b. Cardiac cycle period

Some non-limiting examples of physiological parameters include:

An increase in Breathing Rate:

$$((\text{current}_{breathingrate}) - (\text{resting}_{breathingrate})) = ((\text{resting-current}_{BR}) - (\text{resting}_{BR}))$$

Figure 4A:
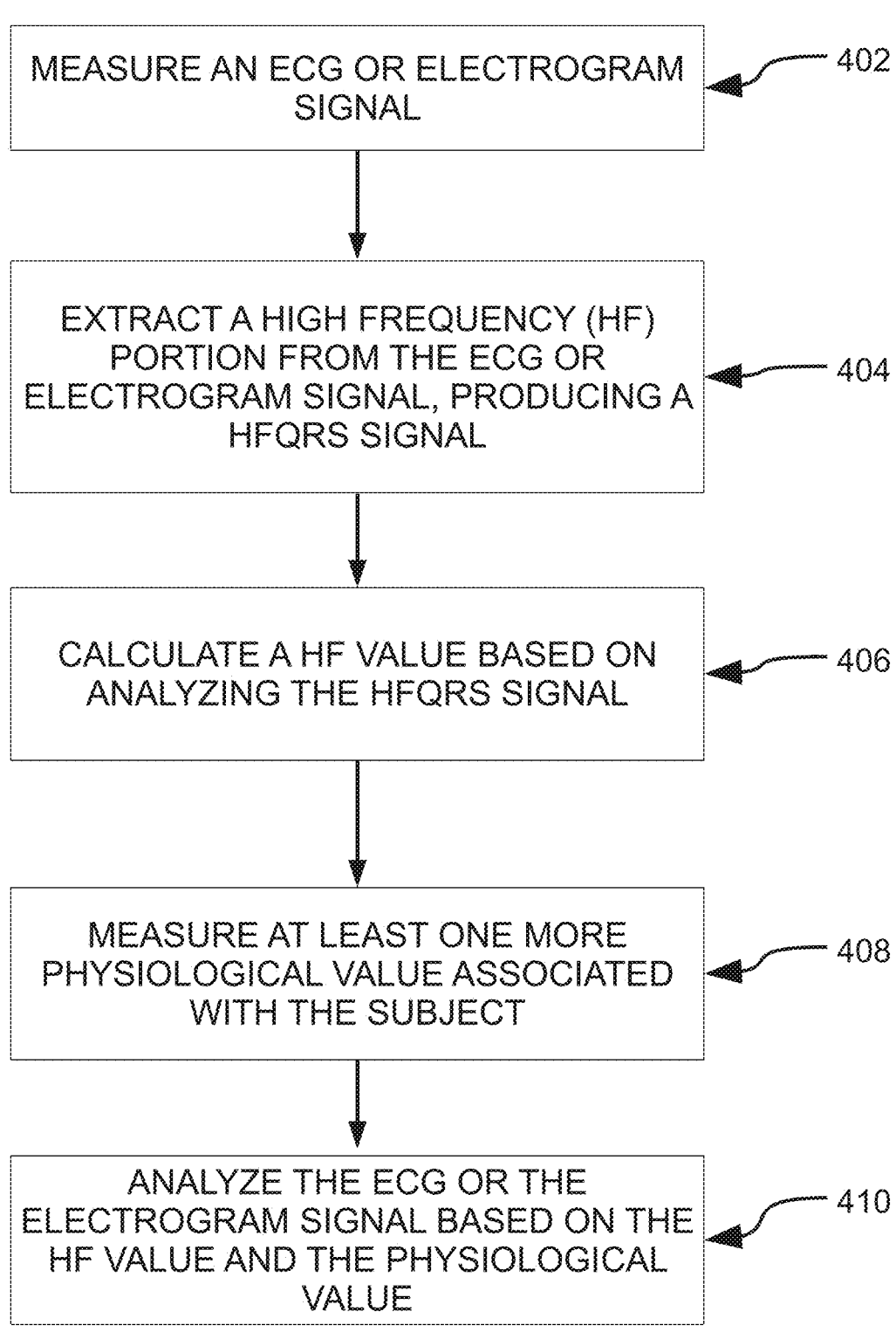
FIG. 4A is a simplified flow chart illustration of a method for analyzing a subject's cardiac condition according to an example embodiment of the invention.

Reference is now made to FIG. 4A, which is a simplified flow chart illustration of a method for analyzing a subject's cardiac condition according to an example embodiment of the invention.

The method illustrated by FIG. 4A includes:

measuring an ECG or electrogram signal (402);

extracting a high frequency (HF) portion from said ECG or electrogram signal, producing a HFQRS signal (404);

calculating a HF value based on analyzing said HFQRS signal (406);

measuring at least one more physiological value associated with said subject (408); and analyzing said ECG or said electrogram signal based on said HF value and said physiological value calculating an adjusted HFQRS signal value based on said HFQRS signal value and said physiological value (410).

In some embodiments, ischemia is indicated in cases where a notable change in the HF signal occurs during a minor change or no change in the physiological condition. By way of a non-limiting example, a 50% relative decrease in HF RMS (for example a decrease from 8 μV to 4 μV) and a heart rate increase of 10% (for example a decrease from 90 to 99 BPM).

Figure 4B:
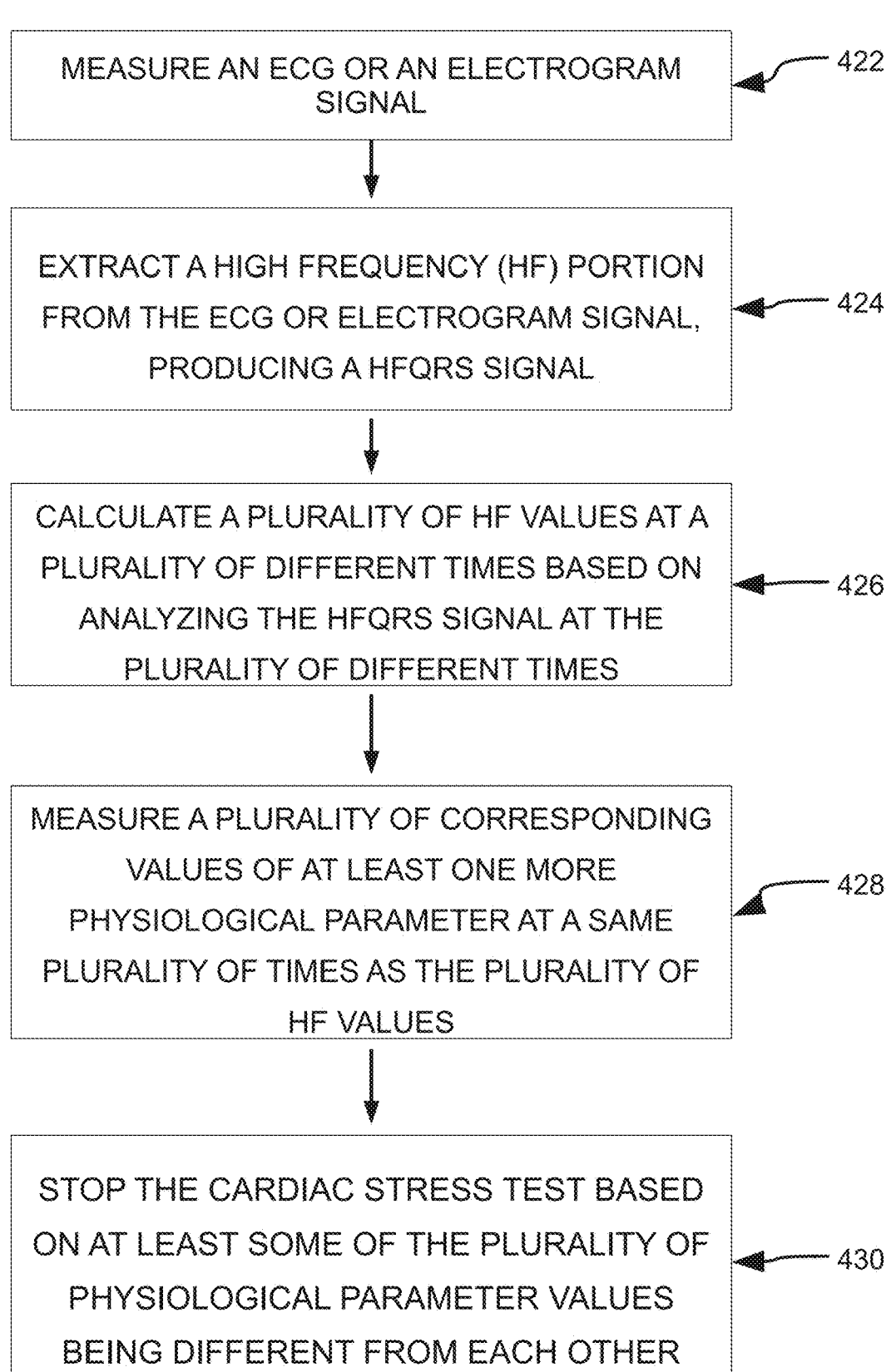
FIG. 4B is a simplified flow chart illustration of a method of performing a cardiac stress test according to an example embodiment of the invention.

Reference is now made to FIG. 4B, which is a simplified flow chart illustration of a method of performing a cardiac stress test according to an example embodiment of the invention.

The method illustrated by FIG. 4B includes:

measuring an ECG or an electrogram signal (422);

extracting a high frequency (HF) portion from the ECG or electrogram signal, producing a HFQRS signal (424);

calculating a plurality of HF values at a plurality of different times based on analyzing the HFQRS signal at the plurality of different times (426);

measuring a plurality of corresponding values of at least one more physiological parameter at a same plurality of times as the plurality of HF values (428); and stopping the cardiac stress test based on at least some of the plurality of physiological parameter values being different from each other (430).

Reference is now made to FIG. 4C, which is a simplified flow chart illustration of a method of analyzing a subject's cardiac condition according to an example embodiment of the invention.

The method illustrated by FIG. 4C includes:

measuring an ECG or an electrogram signal (442);

extracting a high frequency (HF) portion from the ECG or electrogram signal, producing a HFQRS signal (444);

calculating a plurality of HF values at a plurality of different times based on analyzing the HFQRS signal at the plurality of different times (446);

measuring a plurality of corresponding values of at least one more physiological parameter at a same plurality of times as the plurality of HF values (448); and analyzing the ECG or the electrogram signal based on the plurality of HF values and corresponding plurality of physiological values (450).

It is expected that during the life of a patent maturing from this application many relevant devices and methods for measuring electrograms, both low frequency and high frequency, will be developed and the scope of the term electrogram is intended to include all such new technologies a priori.

It is expected that during the life of a patent maturing from this application many relevant devices and methods for measuring electrocardiograms, both low frequency and high frequency, will be developed and the scope of the term electrocardiogram is intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers there-between.

Unless otherwise indicated, numbers used herein and any number ranges based thereon are approximations within the accuracy of reasonable measurement and rounding errors as understood by persons skilled in the art.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Various embodiments and aspects of the present disclosure as delineated hereinabove and as claimed in the claims section below find experimental support in the following examples.

EXAMPLES

Reference is now made to the following examples, which together with the above descriptions illustrate some embodiments of the disclosure in a non-limiting fashion.

Figures 5A, 5B:
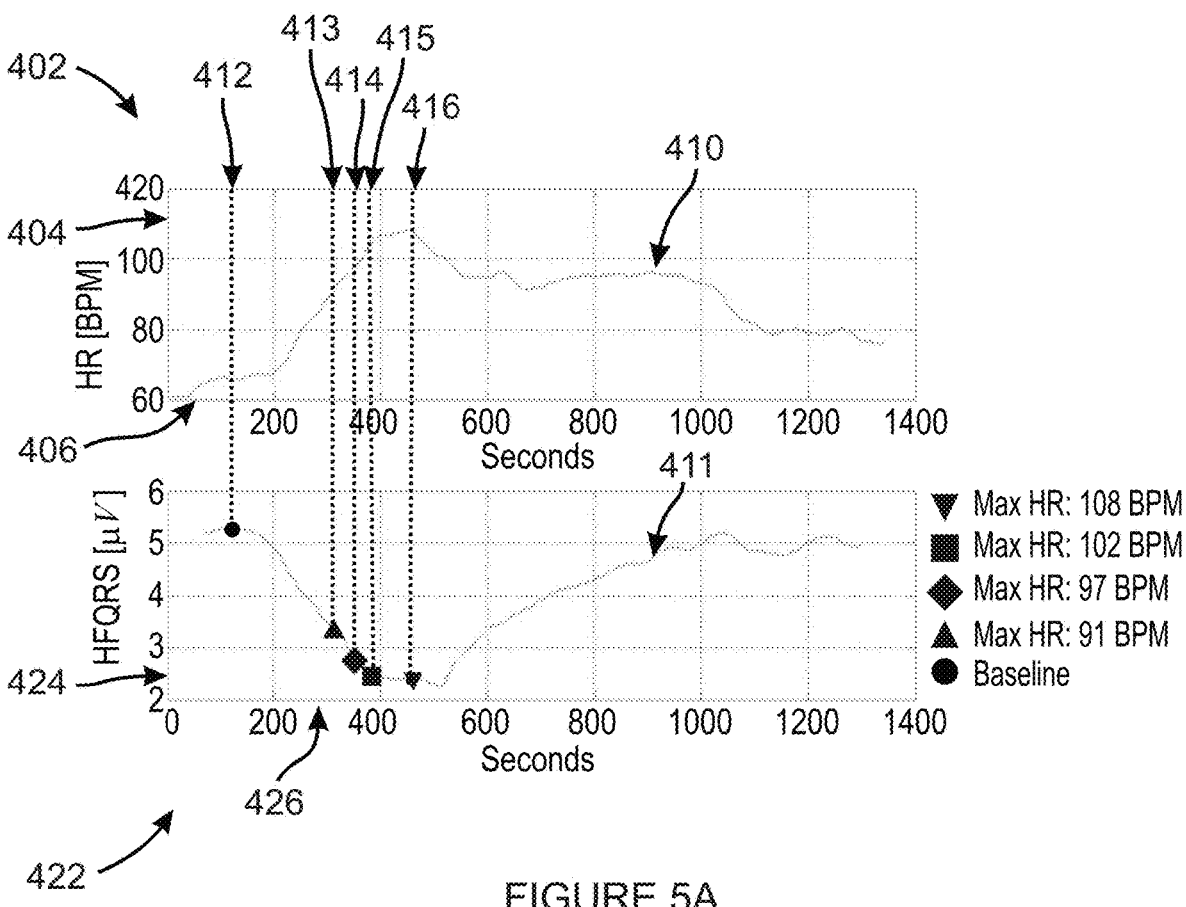
FIG. 5A illustrates a potential advantage of incorporating an HR-adjusted threshold into HFQRS signal analysis, according to an example embodiment.
FIG. 5B shows a table 432 comparing various heart rate (HR) and HFQRS signal values to a baseline heart rate value.

Reference is now made to FIG. 5A, which illustrates a potential advantage of incorporating an HR-adjusted threshold into HFQRS signal analysis, according to an example embodiment.

FIG. 5A shows a heart rate (HR) related trend in HFQRS signal value in a HF signal of a single lead (V4) measured during a conventional 12-lead ECG stress test of an ischemic patient.

FIG. 5A shows a top graph 402 with a Y-axis 404 of HR [beats per minute] and an X-axis 406 of time [seconds], and a bottom graph 412 with a Y-axis 414 of HFQRS signal value [micro-volt] and an X-axis 416 of time [seconds].

FIG. 5A shows a first trace 410 in the top, heart-rate, graph 402, which shows a heart rate of the patient over a duration of the stress test, and a second trace 411 in the bottom, HFQRS signal value, graph 422, which shows HFQRS signal values the HF electrocardiogram signal over the duration of the stress test.

At various points in time 412 413 414 415 416 different symbols indicate varying HFQRS signal values at varying heart rates during the test.

A circle symbol at time 412 indicates where a baseline or resting HFQRS signal value was measured.

An up-side down triangle symbols at time 416 indicates where high HR (considered in this stress test as 100% HR) and a low HFQRS signal value were measured.

Additional symbols at times 413 414 415 indicate different times wherein the patient achieved lower HR (95%, 90%, and 85% of the 100% HR, respectively).

The different times 413 414 415 were taken to simulate different potential test endpoints that were selected to simulate three shorter tests wherein a patient achieved lower heart rates (95%, 90%, and 85% of the 100% HR, respectively).

Using the same baseline, or resting heart rate the HFQRS index was calculated for additional simulated tests as shown in FIG. 5B, which shows a monotonic decrease in HFQRS signal values with decreasing % HR.

Reference is now made to FIG. 5B, which shows a table 432 comparing various heart rate (HR) and HFQRS signal values to a baseline heart rate value.

FIG. 5A is optionally used to benefit from an HR-adjusted threshold for interpreting HF trends. By way of a non-limiting example, looking at the trend in FIG. 5A, it can be seen that if a test was ended before a subject had reached 100 BPM references 413 414 in FIG. 5A), a relative reduction of HFQRS in μV was below a 50% threshold.

FIG. 5A also shows trend behavior for heart rates higher than 100 BPM (references 415 416), and their matching relative reductions in HFQRS. We can conclude that the negative interpretation is wrong. However, if an HR-adjusted threshold that reduce the 50% threshold for patterns that present high reduction at low relative heart rates changes, the true positive interpretation was obtained (see simulated tests indicated by references 413-414.

In addition, table 432 results also show that a HR-adjusted threshold that reduce the constant threshold for 50% decrease in HFQRS levels for positive HFQRS lead, can be valuable to detect the lead as positive and therefore for early diagnosis.

A study is hereby described in which changes in High Frequency Intracardiac Electrograms indicate Myocardial Ischemia Myocardial ischemia (MI) causes electrophysiological changes that are reflected in both a surface electrocardiogram and an intracardiac electrogram (EGM). Recent studies have shown that EGM monitoring of ST segment deviations may be a sensitive marker for thrombotic coronary occlusion. High frequency QRS (HFQRS) of surface ECG has been demonstrated to be a reliable marker of MI. Very little work has been published on the high frequency component of EGM signal, such as those that are measured in implantable devices, as during MI.

The study recorded and analyzed intracardiac HFQRS (iHFQRS) from standard EGM electrodes in typical locations (RV, RA and LV), in normal condition and during MI, in order to study the response of iHFQRS to ischemia in animals.

Methods—Two distinct porcine models were used—acute and chronic. In the acute model, ischemia was induced in an anesthetized swine by inflating a balloon in one of the coronary arteries. In the chronic model a copper plated stent was placed along the LAD artery and the conscious animal was monitored for several weeks while the stent gradually became occluded.

Results—A clear and significant reduction was demonstrated in the amplitude of the iHFQRS signal during balloon-induced MI. The response preceded the change in ST segment and, in short-period occlusions, was the only indicator of ischemia. In the chronic model, the iHFQRS signal was more sensitive to the developing ischemia after the copper plated stent was introduced and was also more stable compared to the ST segment level. Two effects were noticed in the iHFQRS of an ischemic animal: the RMS decreased in periods of increased heart rate (stress test) and the average amplitude on a day-to-day basis presented monotonous decrease with the progression of the induced disease. These iHFQRS changes were noticed several days before an acute MI (AMI) occurred.

Conclusion—The results demonstrate the potential of iHFQRS as an early indication for the onset and progression of Myocardial Ischemia.

Introduction

Early Diagnosis and Monitoring of Ischemic Heart Disease

Diagnosis of ischemic heart disease (IHD), a global leading cause of death, greatly relies on the interpretation of surface electrocardiogram (ECG). However, various abnormalities of depolarization or repolarization phases of the cardiac cycle, caused by myocardial ischemia (MI), are reflected by relatively minor changes in the surface ECG, or may not be apparent at all during visual inspection. Given the variety of available clinical protocols which could reduce mortality, early detection of IHD and ischemic events may substantially improve clinical outcome.

Acute myocardial infarction (AMI), an acute ischemic condition which requires prompt intervention to prevent further myocardial necrosis, is a classic scenario where the time from onset to treatment is crucial and must be shortened as much as possible. Stable IHD, a condition which refers to patients who have no recent or acute changes in their symptomatic status, is another condition where early detection is highly valuable. Stable IHD patients tend to develop chronic, slow worsening angina symptoms, which are often managed medically, or may go on to require urgent intervention and thus urge the need for a continuous, long-term monitoring.

Unlike surface ECG analysis, which is based on changes in the repolarization phase of the cardiac cycle (ST segment changes), HFQRS analysis is based on the HF components of the depolarization phase (QRS complex). While surface ECG signal is measured in millivolts scale, HFQRS extracted from surface ECG are in the microvolts scale ($\mu$V). The extraction of these low-amplitude signals may use high-resolution ECG acquisition, SNR enhancement and advanced signal processing techniques.

The independent nature and of ST-segment and HFQRS makes the latter a potentially valuable tool in the diagnostic process, and adds information that can be used in concert with the ST-segment related information. Furthermore, it has been shown to provide diagnostic information about the existence and severity of acute myocardial infarction and in diagnosing acute coronary syndrome patients in the emergency department.

HFQRS analysis may be utilized to other clinical applications. One such application is to embed the HFQRS analysis in implantable devices, in order to enable monitoring of MI, improve diagnosis of MI-related pathologies and reduce healthcare costs.

Intacardiac Electrograms

Intacardiac electrograms (EGM) refer to sensing intrinsic changes in the electric potential signals measured by electrodes from a specific location on or in the heart. In some embodiments, EGM signals are optionally recorded, analyzed, and stored by electrodes (e.g. of an implantable cardiac device) which allow measuring bipolar records (recorded from two adjacent electrodes (typically within a chamber), and unipolar records (recorded from a tip electrode located within the heart against the device "can", usually located in the upper chest or shoulder). Modern implantable devices have extensive memory and are capable of continuous monitoring of EGM.

In comparison to a surface ECG, where signals are recorded from a body surface, EGM signals are measured from the myocardium. Consequently, EGM records avoid the insulating effects of the thorax and the lungs, and thus, usually have 5-10 times larger amplitude. In addition, they do not contain noise originating from the electrode-skin interface, and are considered more independent of electrode positioning.

Patients with an implanted device, namely a cardiac rhythm management device, have a high prevalence of CAD (Coronary Artery Disease). Several studies have shown that cardiac ischemia can be detected from EGM and that the sensitivity of EGM for detection of ischemia may be superior to that of surface ECG. More recently, the ability of an implantable device to assist in the early diagnosis of acute MI, based on intracardiac ST-segment measurements, was demonstrated in a porcine model and in humans. However, ischemic HFQRS manifestations in EGM signals have not been investigated.

The current study reports animal experiments characterizing changes in intracardiac HFQRS electrogram (iHFQRS) during MI. The investigation was conducted in a preclinical setting, comprised of acute and chronic models. The acute MI model was applied to evaluate the sensitivity and timing of iHFQRS in detecting ischemia in comparison to intracardiac ST-segment deviations. The chronic MI model was based on the implantation of a copper coated stent into the coronary artery and was applied to test the feasibility of identifying the formation of coronary infract using iHFQRS changes, and assess its potential to provide a reliable monitoring of ischemic burden.

Methods

Acute Phase

A prospective, interventional preclinical study was conducted to evaluate the feasibility of an implantable device to provide monitoring and/or early detection of MI. EGM electrodes simulating an implantable bi-ventricular device were implanted in 3 anesthetized and ventilated juvenile (4-6 months) female swine (weight 60-70 Kg) in a controlled environment.

Data Acquisition

EGM were acquired using designated acquisition hardware (AQ-200, BSP medical, Tel-Aviv, Israel), with a modified amplifier (input range ±100 mV) and wiring configuration. This example system is equipped with a high sampling rate of 2 kHz per channel, wide frequency response of up to 300 Hz and high-resolution of 16-bit and therefore, is suitable for HFQRS analysis.

By way of a non-limiting example, rewiring of the system, from conventional 12-Lead ECG wiring configuration, to STAR configuration, was performed to resemble wiring of an implantable pacemaker as follows: six EGM channels were connected to channels C1-C6 (each intra-cardiac electrode was connected to two channels, one for its distal tip and the other for its proximal tip), the can was connected to left-leg channel (LL) and the Neutral was connected to right-leg channel (RL). By using the STAR configuration, six far-field EGM voltage recordings were obtained between each of the electrode tips: (RVd, RVd/p, RAd/p, LVd/p) and the can.

Trial Protocol

Each trial started with an invasive procedure in which three bipolar pacemaker leads were implanted in the: right ventricle (RV), right atrium (RA) and the coronary sinus (CS), to pace the left ventricular (LV), resembling typical implanted intra-cardiac electrode positioning. Each electrode had a proximal and distal tip (henceforth denoted by 'p' and '4:1' at suffix) and thus, in total, six EGM channels were recorded simultaneously. Next, two additional electrodes were implanted subcutaneously: can-simulating electrode (CAN), situated in a can position and used as reference, and another noise cancellation electrode (Neutral). To enable reliable fixation to the heart's tissue both RV and RA electrodes were implanted with extendable and retractable screws (CapSureFix™ 5568, Medtronic and Safio s53, Biotronik respectively) whereas the LV electrode was inserted to the CS and positioned adjacent to the LV wall using a flexible designated electrode (Corox OTW 85-BP, Biotronik). Electrode positioning was validated via fluoroscopy and a real-time visual examination of the EGM signals, triggered by an external pacemaker.

Once all electrodes were properly positioned they were connected to the acquisition device and baseline measurements were recorded. After a satisfactorily adequate baseline recording was registered, a balloon catheter was inflated at different sites along the coronary artery, in one or more major artery, to produce partial and complete occlusions. Partial and complete balloon occlusions of the major coronary arteries (LAD, LCX and RCA) were used to induce AMI. Table 1 (see below) lists occlusion locations and the number of repetitions per animal. Occlusions varied in location along the coronary, in severity (complete or partial) and in duration (occlusions duration ranged between 10 and 180 seconds). Each occlusion started with several minutes of baseline recording prior the balloon inflation and continued after balloon deflation without any intervention (>10 minutes).

TABLE 1

| List of occlusions per location | | | | | |
|---|---|---|---|---|---|
| Coronary Occluded | Occlusions Type | Total Repetitions | Animal No. | Repetitions (#) | Duration (s) |
| LAD Distal | Complete | 6 | 2 | 2 | ~60 |
| | | | 3 | 4 | ~60 |
| LAD Mid | Partial | 3 | 1 | 3 | ~200 |
| Cx Mid | Complete | 9 | 2 | 3 | ~35 |
| | | | 3 | 6 | ~35 |
| RCA mid | Partial | 3 | 2 | 3 | ~50 |

24

HFQRS Analysis

In order to extract the iHFQRS content from the EGM recordings, a three-stage procedure was applied: (1) peak detection (PD), (2) alignment, (3) filtering out low-frequency band, to achieve a high frequency band signal. Since SNR levels were sufficient during records (>10) the analysis was performed in an automatic beat-to-beat analysis approach.

1. Peak detection (PD): an example procedure was based on finding maximum points with amplitude above an updating threshold. A first step was to apply two median filters, one to remove baseline (for example a 301 [ms] window) and the other to suppress T-wave components by subtracting the filter output from the input signal (for example a 151 [ms] window). Next, another median filter (for example a 13 [ms] window) was used in order to eliminate spikes from non-physiologic sources (such as electrode movement) and an absolute value of the signal was sent to the peak detector (some leads have a negative polarity). The peak detector potentially finds a maximum point with amplitude above an adaptive threshold which was initially set, optionally manually and optionally updated iteratively, relatively to the template average. The PD was applied for each lead separately, and optionally only QRS complexes that were detected in at least 2 leads (within a time window of, for example, 30 ms) were considered valid. The detected peak timings were optionally projected to all available leads automatically and used to calculate the heart rate (HR) rate.

2. Alignment: Accurate alignment of the QRS complexes is used for a successful HFQRS analysis. Hence, to optimize alignment, a mid-frequency range template matching procedure was applied to the detected QRS complexes, to achieve a better location of a reference point on the QRS cross-correlation. To that end, raw signals were optionally filtered with a causal finite impulse response (FIR) band pass filter (BPF) with cutoffs of, for example, 20-70 Hz (filter order 21) and a group of adjacent valid QRS complexes from baseline were aligned and averaged to comprise templates for each lead. In EGM the QRS complex may also be referred as a V-wave. The template matching was based on a cross-correlation value between an updating template and a given QRS complex (both, for example, of 200 ms size). An initial template for each lead was constructed from 100 valid complexes. Templates were updated iteratively during recording where each new complex was being compared to the current template and, if inclusion criteria were met, was used to update the template. The templates were then used twice, once as reference to align a valid template with an updating template, based on cross-correlation values, and secondly to exclude irregular complexes. A cross-correlation value between the template and each of the detected complexes (per lead) was used as the inclusion metric with an optional threshold of <0.95 as an exclusion criterion. An outcome of this stage was the timing of all the valid QRS complexes and their matching lags for the optimized alignment.

3. Filtering to the high frequency band: For filtering to the HF frequency band, a designated digital filter was used. The filter was applied for all records and leads prior to quantification. Next, valid QRS complexes were extracted using a, for example, 200 ms time window centered on each of the valid QRS complexes. To further optimize the alignment, a high resolution correction, based on a parabolic approximation, was applied.

HFQRS Assessment

Two approaches were used to assess the iHFQRS during normal perfusion and during occlusion: a morphological examination and a quantification. To visually examine the iHFQRS signals, the complexes' envelops were calculated using a Hilbert transform, used for valid complexes only. Since the iHFQRS signal oscillates rapidly, the envelop representation is more efficient and useful for analysis and comparison. To quantify the HFQRS content, the root mean square (RMS) of the iHFQRS signal along the QRS complex was calculated. This quantification was applied to valid complexes and used to construct the iHFQRS time curves. These time curves describe the levels of the iHFQRS over the course of the experiment (per lead) and are used to assess the time-dependent sensitivity of iHFQRS indexes in identifying MI.

Conventional ECG Analysis

To compare HFQRS time-dependent sensitivity to indexes derived from the conventional EGM, ST segment deviations were automatically extracted for the valid complexes and a matching ST segment time curves were produced. A low frequency RMS value was calculated for the QRS complexes and the ST deviation was defined as a difference between the ST level and the PR interval level of the complexes.

Chronic Phase

Experiment Protocol

A series of 5 experiments, varied between 1-2 months, were conducted on a conscious female swine (weight 60-70 Kg), with EGM monitoring 24 hours a day. In order to produce a gradual occlusion formation in the LAD, a copper plated stent was implanted into the artery after a baseline signal of few days was acquired. Stenosis progression was evaluated with several angiography procedures along the experiment.

To identify occlusion formation with iHFQRS signals, two main analysis approaches were examined: (1) elevated HR analysis—this method is based on signals measured during the stress tests that were performed each day (between 1 and 3). A rationale is that in partial occlusion the animal may experience demand ischemia during elevated HR, which could be reflected in a reduction of the iHFQRS signal with respect to the baseline signal (normal HR). (2) Long term iHFQRS analysis—in this approach mean values and standard deviation of the HFQRS signals are examined in segments of an hour or a day, in order to identify a reduction trend in the HFQRS signal values that correlates to the stenosis progression. The above-described method is a non-related HR analysis. Similar analysis approaches were applied to ST segment measurements and the performance between both markers in detecting ischemia were compared.

Data Acquisition

Similarly to the acute model procedure, Intracardiac bipolar pacemaker leads were placed in the LV RV and RA, subcutaneous electrode, in a CAN position, was used as reference lead and another subcutaneous electrode was used for noise cancellation (Neutral). Continuous measurements of the signals were utilized with a six channel Holter monitor—a portable acquisition device and especially designed for this project (manufactured by the Beecardia Company, Haifa, Israel). The Holter was positioned on the back of the animal with a tailored vest. Signals were acquired with high sampling rate (1 KHz) and were recorded to an internal memory card, which was unloaded once a day.

Bluetooth communication to a laptop computer was also available, offering signal monitoring in real time.

Results

Acute Phase

Electrode Positioning

All bipolar electrodes were implanted successfully in all three animals, in the following order: RV, RA and LV. The animals underwent a series of consecutive occlusions: 12, 13 and 2. Occlusions were conducted along the LAD, CRX and RCA respectively. Fluoroscopy and visual assessment were conducted repeatedly to ensure correct electrode positioning.

EGM Records—Validation

EGM signals were recorded during baseline from all animals and from all three leads simultaneously.

Figure 6:
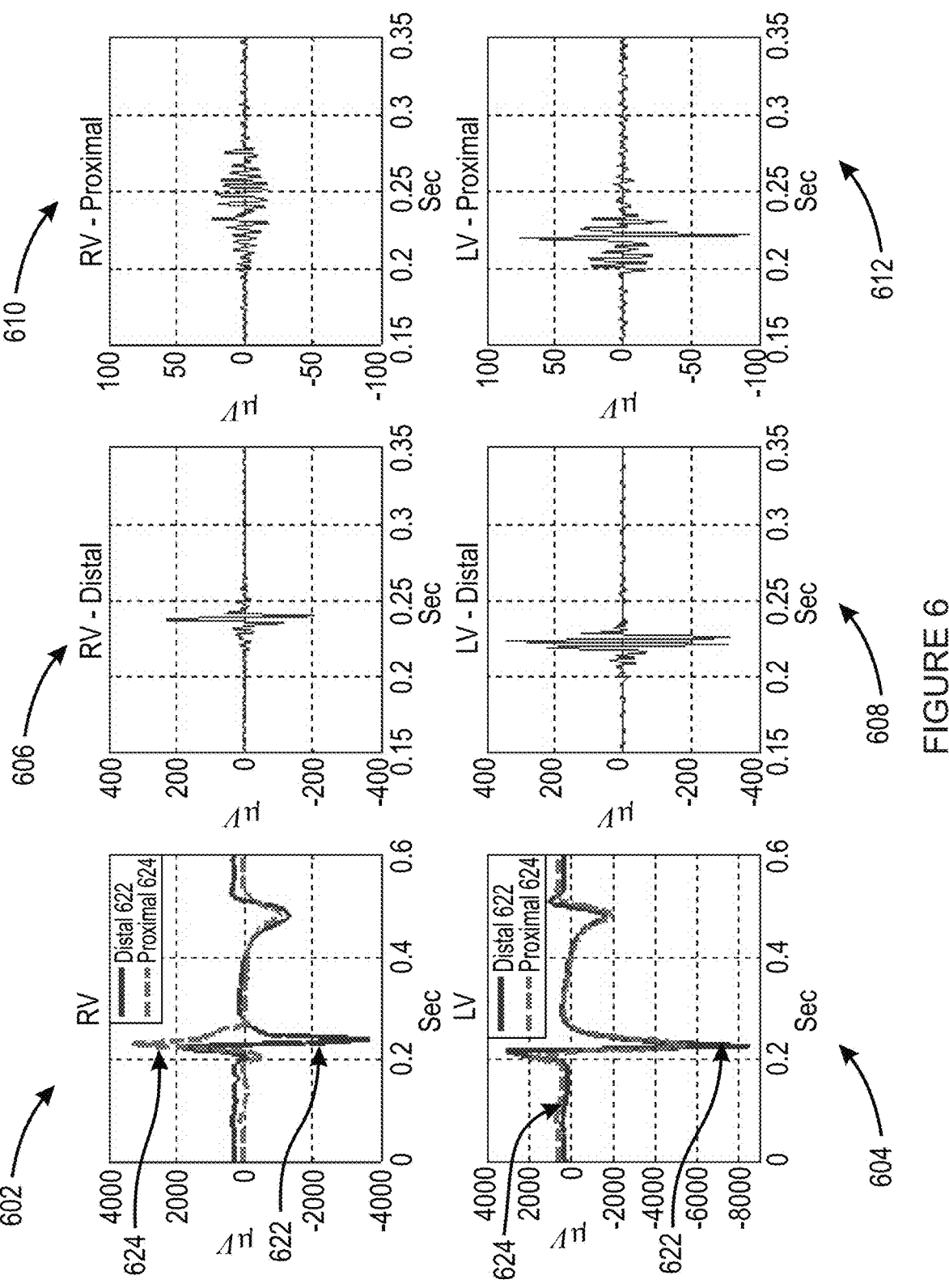
FIG. 6 shows graphs of results from an acute phase of an experiment according to an example embodiment.

Reference is now made to FIG. 6, which shows graphs of results from an acute phase of an experiment according to an example embodiment.

Two graphs 602 604 on a left column of FIG. 6 depict recorded EGM signals from distal 622 and proximal 624 tips of the RV (top graph 602) and LV (bottom graph 604) electrodes during baseline.

An example for the high frequency (HF) content of the EGM signals' after the filtration to the HF band (graphs 606 610 show right ventricle (RV) and graphs 608 612 show left ventricle (LV)).

Graphs 602 604 depict recorded EGM signals from distal and proximal tips of the right ventricle (RV) (graph 602) and coronary sinus (CS) (graph 604) electrodes at normal perfusion. Although they do not have the same morphology, depolarization and repolarization complexes (representing the QRS and T-wave complexes in the conventional ECG) are aligned in time and are clearly visible. EGM voltage is on the order of several millivolts, with the CS distal tip presenting the largest peak-to-peak amplitude, of almost 11 millivolts. In comparison to EGM recorded from proximal tips, a greater signal amplitude was measured from the distal tips (from RV and LV electrodes). Stable EGM signals from the right atrium were measured in the RA channels (both distal and proximal) while presenting a dominant amplitude during atrial contraction and relatively smaller fluctuations during ventricular depolarization phase.

An example of iHFQRS signals extracted from the EGM signals recorded from the distal and proximal tips during baseline is presented in graphs 606 608 610 612. These signals present significantly lower amplitudes (ranging from dozens to hundreds of microvolts) in comparison to the low frequency signals, even during depolarization time frame (at about 70 ms), whereas outside of this time frame they are hardly detected.

Graphs 602 604 show an example of electrogram (EGM) signals measured from distal and proximal tips (continuous 622 and dashed 624 lines, respectively). Graphs 606 608 610 612 show an example of high frequency (HF) content of the EGM signals after filtration to the HF band (graphs 606 610 show the right ventricle (RV) and, graphs 608 612 show the left ventricle (CS)).

Although they do not have same morphology, depolarization and repolarization complexes (representing the QRS and T-wave complexes in the conventional ECG) are aligned in time and are clearly visible between the electrodes and tips. EGM voltage is of the order of several millivolts, with the LV distal tip presents the largest peak-to-peak amplitude, of almost 11 millivolts. In comparison to EGM recorded from proximal tips, greater signal amplitude was measured from the distal tips (from RV and LV electrodes). In addition, both RAd and RAp signals were measured successfully while presenting a dominant amplitude during atrial contraction and relatively smaller fluctuations during depolarization phase.

HFQRS Analysis

Beat-to-beat HFQRS analysis was applied to the EGM signals from all leads and from all three animals. The intensity of the iHFQRS signal and the morphology of iHFQRS signal during normal perfusion (i.e. baseline) and during balloon occlusion were examined and compared to the conventional ST-segment analysis.

An example of iHFQRS signals extracted from the EGM signals (recorded from distal and proximal tips) during baseline is presented in FIG. 6, graphs 606 608 610 612 in the middle and right columns in FIG. 6. The signals have significantly lower amplitude comparatively to the recorded signals (ranged between dozens or hundreds of microvolts), and are oscillate rapidly during the depolarization time frame (around 70 ms), whereas outside of this time frame the signals are hardly detected. In addition, the HF signals recorded from the distal tips have grater amplitude (around 4-fold greater) in comparison to the proximal leads.

The iHFQRS time curves presented a significant reduction in intensity and morphological changes in envelope during occlusions, and in the comparison between perfusion and reperfusion periods. Both RV and LV leads showed iHFQRS sensitivity to ischemia induced by occlusions in several locations. The phenomenon was similarly evident for occlusions in all major arteries: LAD, RCA and LCX, including in cases of distal locations and for very short occlusions (see Table 2 below). The table is marked with "+" where indicates a response, and "−" indicates no response.

TABLE 2

Indication of iHFQRS vs. ST response for occlusions at different coronaries

| | ST | | | iHFQRS | | |
|---|---|---|---|---|---|---|
| RA | CS | RV | RA | CS | RV | Occlusion location |
| — | 2/6 | 6/6 | — | 4/6 | 6/6 | LAD distal |
| 3/3 | — | 3/3 | 3/3 | — | 3/3 | LAD mid |
| — | 8/9 | 4/6 | — | 9/9 | 5/6 | Cx mid |
| — | 0/3 | 2/3 | — | 0/3 | 3/3 | RCA mid |
| 3/3 | 10/18 | 15/18 | 3/3 | 13/18 | 17/18 | Total |

Reference is now made to FIG. 7A, which shows two graphs of significant response, of both ST and iHFQRS signals according to an example embodiment.

FIG. 7A shows significant response, of both the ST signal (top graph 702) and the iHFQRS signal (bottom graph 704), during two sequential, relatively long (>40 seconds) complete occlusions in the LAD.

FIG. 7A shows a first line 701 showing an absolute ST segment deviation (top graph 702) and a second line 705 showing the HFQRS signal (bottom graph 704) recorded from the distal tip of the right ventricle lead (RVd) during two complete occlusions (50 and 70 sec respectively) located along the left coronary artery (LAD). Vertical lines 706 indicate balloon inflation timing, and vertical lines 708 indicate balloon deflation timing.

As can be seen, significant relative decreases of 28% and 40% (equal to absolute values of 7 µV and 10 µV respectively) were observed in the RMS of the iHFQRS together with major ST deviations of 100 µV and 200 µV during first and second occlusions, respectively. As oppose to the RV and LV, the RA signal did not show sufficient sensitivity in most of the measurements and thus is not demonstrated here.

Reference is now made to FIGS. 7B and 7C, which show two graphs depicting if an electrogram and a HFQRS envelope during occlusion according to an example embodiment.

FIGS. 7B and 7C show plots 722 723 724 of a recorded electrogram (graph 720) and a HFQRS signal envelope 742 743 744 (graph 740) at different stages of a first occlusion: before—691 sec (722 742), at an early stage—724 sec (723 743) and towards an end of the occlusion—754 sec (724 744).

ST-segment analysis showed significant deviations during most occlusions. However, usually the iHFQRS response was significantly faster to appear—while no visible change appeared in the recorded EGM signal (including ST segment, T-wave and QRS amplitude), a marked reduction was already observed in the iHFQRS signal.

FIGS. 7B and 7C show a single-beat comparison between the recorded EGM signal and the iHFQRS signal envelope at different time points during an occlusion. In FIGS. 7B and 7C, the EGM morphology remains almost unchanged after 20 seconds of occlusion (lines 722 723 in graph 720), whereas the iHFQRS envelope is significantly reduced (lines 742 743 in graph 740). Yet, after 50 seconds both signals present a significant change—an ST segment elevation and a marked reduction in the iHFQRS envelop (lines 722 724 in graph 720 and lines 742 744 in graph 740).

Figure 8:
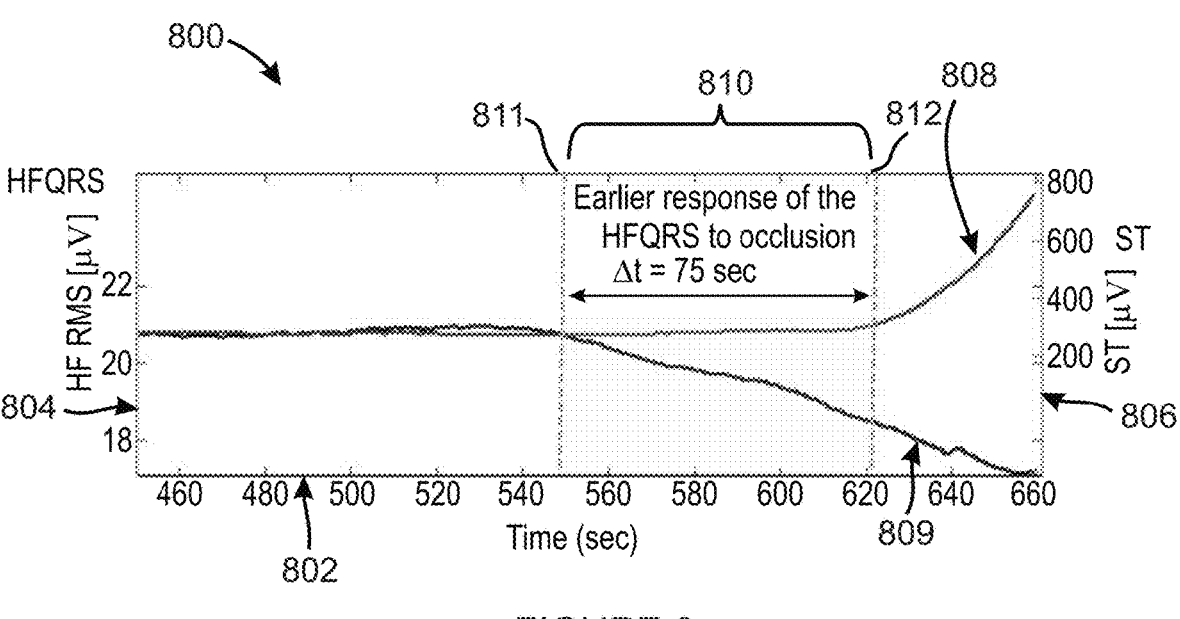
FIG. 8 shows a graph comparing sensitivity of an iHFQRS signal and ST deviations during occlusion according to an example embodiment.

Reference is now made to FIG. 8, which shows a graph comparing sensitivity of an iHFQRS signal and ST deviations during occlusion according to an example embodiment.

FIG. 8 shows a graph 800, with an X-axis 802 showing time in seconds, a left Y-axis 804 showing HFQRS in µV, and a right Y-axis 806 showing ST deviations in µV.

FIG. 8 compares sensitivity of a iHFQRS signal 809 and ST deviations 808 during a long (3 minute) partial occlusion along a distal segment of the LAD in terms of time curves and shows that a significant change in iHFQRS signal 809 was detected 75 seconds 810 prior to the observable ST deviation.

FIG. 8 shows an example for the early response of the HFQRS signal 809 to ischemic condition in comparison to ST segment deviation 808. A left 811 and right 812 vertical dotted line indicate the balloon inflation timing and the timing where a significant deviation in the ST signal was noticed, respectively.

Figure 9:
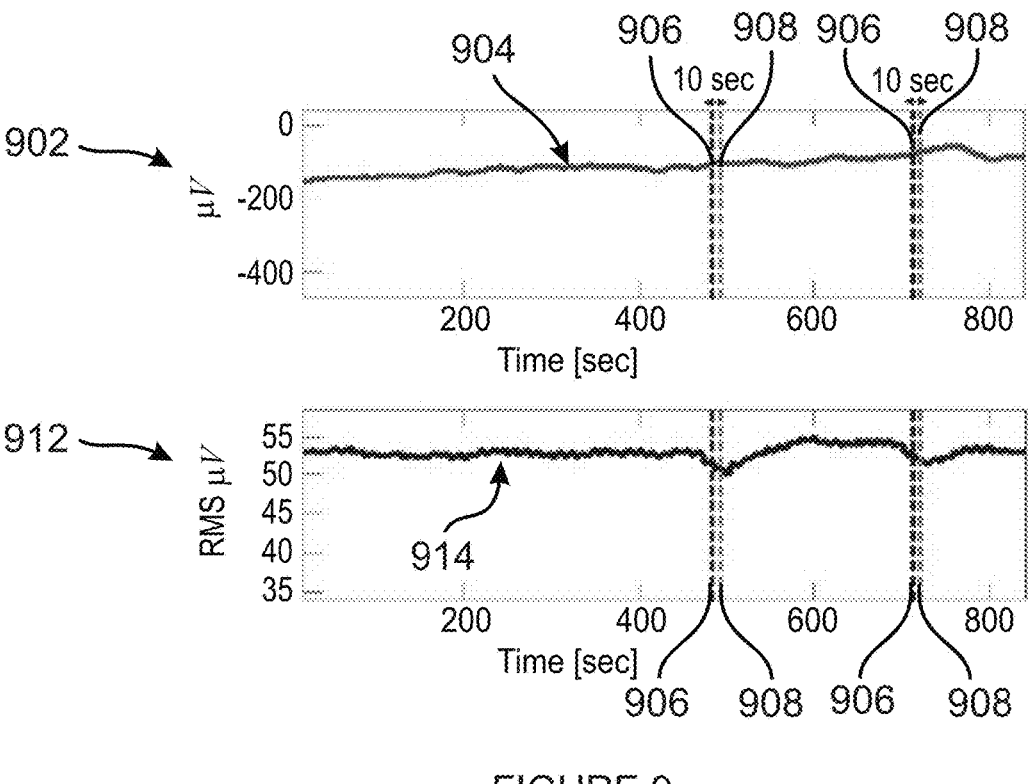
FIG. 9 shows two graphs comparing ST deviation and iHFQRS during two occlusions according to an example embodiment.

In some of the >30 second long occlusions, the deviations 808 were minor comparing to HFQRS analysis, and in some short occlusions, only iHFQRS responded when no ST deviation was detectable (see FIG. 9 as an example).

Reference is now made to FIG. 9, which shows two graphs comparing ST deviation and iHFQRS during two occlusions according to an example embodiment.

FIG. 9 shows a first graph 902, showing ST deviation 904, and a second graph 912 showing iHFQRS 914.

The ST deviation 904 and the iHFQRS 914 time curves were recorded from the left ventricular distal lead (LVd) during two short (10 second each) complete occlusions in a distal segment of the CRX (left circumflex coronary artery).

Vertical lines indicate balloon inflation 906 and deflation 908 respectively.

Figure 10A:
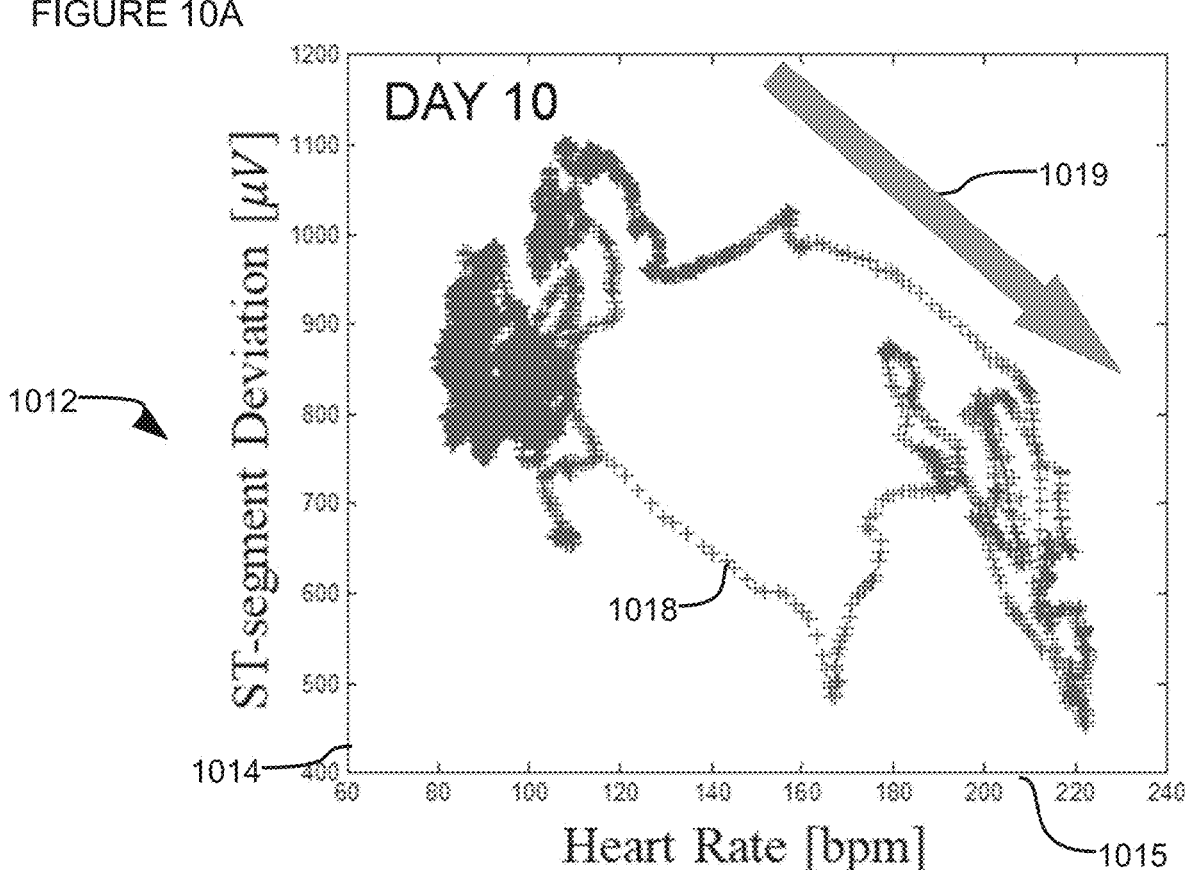
Figure 10C:
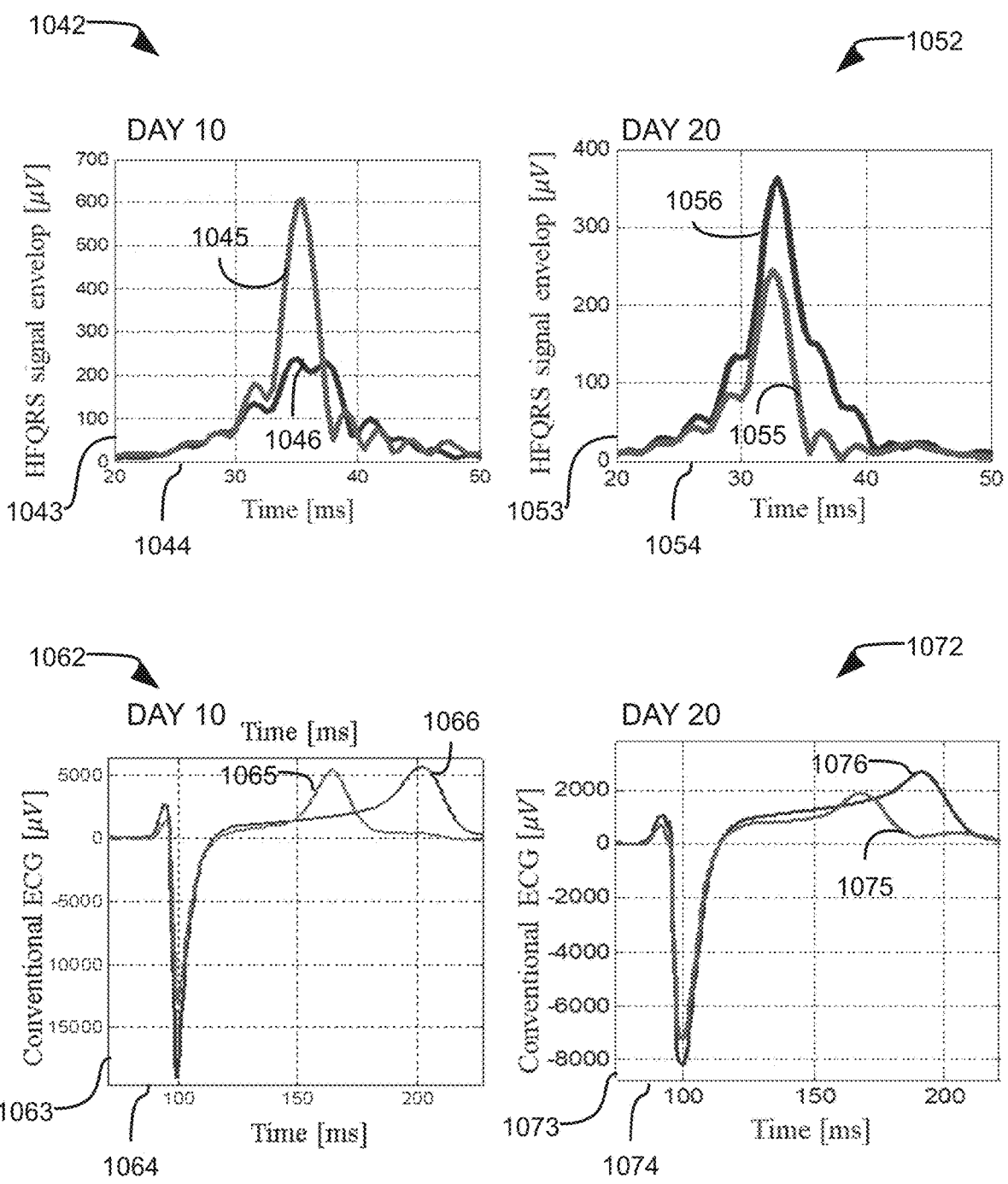

Reference is now made to FIGS. 10A-10C, which are graphs according to an example embodiment showing ST and HFQRS signal values collected during an induced ischemia episode.

FIG. 10A shows a first graph 1002 which has an X-axis 1005 of heart rate and a Y-axis 1004 of intra-cardiac HFQRS (iHFQRS) signal value in micro-volts [μV].

The first graph 1002 shows a scatter plot 1008 of iHFQRS signal values VS heart rate values collected over a period of time, by way of a non-limiting example over a day, in which ischemia had not yet been induced. During that period of time the subject of the experiment was caused to exercise, causing differences in heart rate over time.

The first graph 1002 shows that in a non-ischemic subject, the iHFQRS signal value rises as the heart rate rise. A line 1009 drawn in the first graph 1002 is approximately parallel to a regression line which can be calculated for the points in the scatter plot 1008.

FIG. 10A also shows a second graph 1012 which has an X-axis 1015 of heart rate and a Y-axis 1014 of ST signal value in micro-volts [μV].

The second graph 1012 shows a scatter plot 1018 of ST values VS heart rate values collected over the same period of time as the first graph 1002.

The second graph 1012 shows that in a non-ischemic subject, the ST signal value lowers as the heart rate rises. A line 1019 drawn in the second graph 1012 is approximately parallel to a regression line which can be calculated for the points in the scatter plot 1018.

FIG. 10B shows a third graph 1022 which has an X-axis 1025 of heart rate and a Y-axis 1024 of iHFQRS signal value in micro-volts [μV].

The third graph 1022 show a scatter plot 1028 of HFQRS signal values VS heart rate values collected over a period of time, by way of a non-limiting example over a day, in which the subject had induced ischemia. During that period of time the subject of the experiment was caused to exercise, causing differences in heart rate over time.

The third graph 1022 shows that in an ischemic subject, the HFQRS signal value lowers as the heart rate rise. A line 1029 drawn in the third graph 1022 is approximately parallel to a regression line which can be calculated for the points in the scatter plot 1028.

FIG. 10B also shows a fourth graph 1032 which has an X-axis 1035 of heart rate and a Y-axis 1034 of ST signal value in micro-volts [μV].

The fourth graph 1032 is a scatter plot 1038 of ST values VS heart rate values collected over the same period of time as the third graph 1022.

The second graph 1032 shows that in a non-ischemic subject, the ST signal value lowers as the heart rate rises. A line 1039 drawn in the fourth graph 1032 is approximately parallel to a regression line which can be calculated for the points in the scatter plot 1038.

Comparing the second graph 1012 to the fourth graph 132 shows that the ST signal scatter plots lower as heart rate rises both in a non-ischemic subject and in an ischemic subject.

Comparing the first graph 1002 to the third graph 122 shows that the iHFQRS signal scatter plot in a non-ischemic subject rises as heart rate rises, while the iHFQRS signal scatter plot lowers in an ischemic subject as heart rate rises.

In some embodiments, pairs of values of HFQRS signal and heart rate are measured at various points in time, and a relation between HFQRS signal values and heart rate is estimated.

In some embodiments, if HFQRS signal value do not increase when heart rate increase, an indication of potential ischemia is produced.

In some embodiments, if HFQRS signal value decreases when heart rate increase, an indication of potential ischemia is produced.

In some embodiments, a regression line is calculated for the pairs HFQRS and heart rate values.

In some embodiments, if a slope of the regression line is not positive, an indication of potential ischemia is produced.

In some embodiments, if a slope of the regression line is negative, an indication of potential ischemia is produced.

It is noted that the downward sloping line of the third graph 1022 may be detected using only a lower-heart-rate portion of the scatter plot 1028.

In some embodiments, an indication of potential ischemia is potentially detected in a scatter plot 1028 of HFQRS signal values VS heart rate values collected over a period of time in a subject who has not achieved maximal heart rate planned and/or allowed for the subject.

By way of one non-limiting example, a subject may start to undergo a standard six-minute test, or a Bruce Test, or a similar stress test, and an indication of potential ischemia may be obtained by using a scatter plot 1028 of HFQRS signal values VS heart rate values, before the end of the test according to current practice.

By way of another non-limiting example, a subject may go about his/her normal activities, be they strenuous enough to reach a stress heart rate or not, and an indication of potential ischemia may be obtained by using a scatter plot 1028 of HFQRS signal values VS heart rate values, based on collect HFQRS signal values at various heart rate values.

In some embodiments, an Implantable Cardiac Device (ICD) may optionally collect pairs of HFQRS signal values and heart rate values based on analyzing cardiac signals over a period of time, and potentially produce an indication of potential ischemia.

In some embodiments, the period of time may be short— optionally a few minutes, optionally automatically selected by the ICD as soon as a sufficient range of heart rate has been collected.

In some embodiments, the ICD optionally calculates a rolling slope-of-regression line value of pairs of HFQRS signal values and heart rate values, adding a newest pair and removing an oldest pair of values.

In some embodiments, the ICT optionally produces an indication of potential ischemia when the rolling slope of the regression line reaches below a threshold value.

In some embodiments, the ICT optionally produces an indication of potential ischemia when the rolling slope of the regression line reaches a specific percentage below a base threshold value of the rolling slope.

In some embodiments, the base threshold value of the rolling slope is optionally produced during a medical examination or a stress test as described above, when a physician optionally decides the base value represents a reasonable, non-ischemic value.

In some embodiments, the base threshold value of the rolling slope is optionally an initial value produced when the ICD starts such measurements and analysis, and serves as the base value from then on.

In some embodiments, the base threshold value of the rolling slope is optionally determined by a physician, optionally adjusted when a subject presents an indication of potential ischemia based on the rolling slope, and the physician determined that the subject is not ischemic.

FIG. 10C shows four graphs 1042 1052 1062 1072.

The four graphs are of the same subject as described with reference to FIGS. 10A and 10B, and show values measured on the same days, before (graphs 102 1062) and after (graph 1052 1072) inducing ischemia FIG. 10C shows a first graph 1042 and a second graph 1052 showing values of an HFQRS signal VS time, during a short period of time during a heartbeat when the HFQRS signal is highest.

The first graph 1042 has an X-axis 1043 in μV, and a Y-axis 1044 in mSec. The second graph 1052 has an X-axis 1053 in μV, and a Y-axis 1054 in mSec.

FIG. 10C also shows a third graph 1062 and a fourth graph 1072 showing values of an ECG signal during one heartbeat VS time.

The third graph 1062 has an X-axis 1063 in μV, and a Y-axis 1064 in mSec. The fourth graph 1072 has an X-axis 1073 in μV, and a Y-axis 1074 in mSec.

It is noted that the X axes 1044 1054 of the first graph 1042 and second graph 1052 are not aligned to the X axes 1064 1074 of the third graph 1062 and the fourth graph 1072.

The first graph 1042 shows a first line 1045 which is associated with a higher heart rate of 205 beats per minute (bpm), and a second line 1046 which is associated with a lower heart rate of 115 bpm, of the non-ischemic subject. The first graph 1042 shows an agreement with what the graph 1002 of FIG. 10A shows, that a higher HFQRS signal value is associated with a higher heart rate in a non-ischemic subject.

The second graph 1052 shows a first line 1055 which is associated with a higher heart rate of 215 bpm, and a second line 1056 which is associated with a lower heart rate of 90 bpm, of the subject after ischemia was induced. The second graph 1052 shows an agreement with what the graph 1012 of FIG. 10A shows, that a higher HFQRS signal value is associated with a lower heart rate in an ischemic subject.

The third graph 1062 shows a first line 1065 which is associated with a higher heart rate of 205 bpm, and a second line 1066 which is associated with a lower heart rate of 115 bpm, of the non-ischemic subject. The third graph 1062 shows a difference between the heart rates—the heartbeat line is shorter in time for the higher heart rate, and does not show a significant difference in amplitude between the higher heart rate first line 1065 and the lower heart rate second line 1066.

The fourth graph 1072 shows a first line 1075 which is associated with a higher heart rate of 215 bpm, and a second line 1076 which is associated with a lower heart rate of 90 bpm, of the subject after ischemia was induced. The fourth graph 1072 shows a difference between the heart rates—the heartbeat line is shorter in time for the higher heart rate, and also shows a difference in amplitude between the higher heart rate first line 1075 and the lower heart rate second line 1076.

Chronic Phase

The model succeeded to create a rapid gradual progression in stenosis around the lesion.

In some animals occlusion progressed faster than expected, for example the coronary diagonal was completely occluded only 14 days after stent implantation, and a complete occlusion of the LAD was achieved 24 days after implantation.

In Animal 1, although a distinguish baseline was not acquired, a clear indication of ischemic condition was observed with the iHFQRS stress analysis (LVp). Demand ischemia was observed 13 days before the first MI, when LAD was partially occluded.

Animal 3 also showed a clear transition in the iHFQRS responses (RVd) between the baseline measurements and the post-stent implantation period; a transition that was also correlated to the stenosis progression.

In Animal 4, although the occlusion was not evolved properly (with MI immediately after implantation), there was a clear reduction in the iHFQRS after the implantation. Animal 5 also showed a clear transition in the iHFQRS response during the course of the experiment.

HFQRS Analysis

Discussion

Acute Model

The results presented here demonstrate significant reduction in the intensity of the HFQRS during occlusions, compared to the perfusion and reperfusion periods. This phenomenon appeared during occlusions in all major arteries: LAD, RCA and LCX, including distal locations.

ST segment presented detectable deviations during occlusions. However, HFQRS responses was usually significantly faster to appear: when no changes appeared in the LF signal, including ST segment, T-wave and QRS amplitude, a significant reduction was already observed in the high frequency signal; Indicating that HFQRS is a more sensitive marker, or equivalently that the ischemic mechanism in its earlier stages is expressed in the high frequency components of the signal. These phenomena can be further viewed in the context of the chronic study, were iHFQRS responses were measured in earlier stages of the occlusion formation than the ST responses.

The results indicate that iHFQRS is a sensitive marker for detecting gradual occlusion evolvement in the presence of ischemic burden. The stress analysis results were generally consistent and showed good responses in all animals which were correlated to the animal clinical condition.

In addition to the response timing, in some measurements (usually on very short occlusions) only HFQRS responses were measured without ST deviations.

Both RV and LV leads showed HFQRS sensitivity to ischemia induced from several occlusion locations. However, not enough occlusion sessions were conducted in order to map the relationship between occlusion location and those leads.

The results of this preliminary study suggest that the iHFQRS component of the intracardiac signal can produce a sensitive fingerprint for myocardial ischemia, or equivalently, that the ischemic mechanism in its earlier stages is expressed only in the high frequency band of the signal.

The results also demonstrate the advantages of this approach over conventional ST analysis in term of sensitivity.

The fact that the significant change in the iHFQRS morphology and in time curve appeared before the change in the EGM (between approximately 20-45 and 40-85 seconds in complete and partial occlusions respectively) indicate that HFQRS signal is a more sensitive marker for ischemic condition.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of analyzing a subject's cardiac condition, implemented by an implantable device, wherein said implantable device comprises at least one electrode and a processor connected to said at least one electrode, said at least one electrode is placed on a body of said subject, and the method comprises:

measuring, by said at least one electrode, an electrocardiogram (ECG) or an electrogram signal;

extracting, by said processor, a high frequency (HF) portion in a frequency range of 150 Hz to 250 Hz from a QRS portion of said ECG or electrogram signal, to produce a HFQRS signal;

calculating, by said processor, a HF value comprising a root mean square (RMS) of said HFQRS signal based on analyzing said HFQRS signal;

measuring, by said at least one electrode, at least one more physiological value associated with said subject;

analyzing, by said processor, said ECG or said electrogram signal based on said HF value and said physiological value to determine whether said subject is ischemic, comprising:

producing, by said processor, a scatter plot of a plurality of points, each point defined by a pair of a first value of said HF value and a second value of said physiological value;

calculating, by said processor, a slope of a regression line passing through the plurality of points in the scatter plot; and determining, by said processor, a likelihood of ischemia based on said slope; and in response to said subject being ischemic, producing, by said processor, an indication of ischemia to a physician, to thereby perform prompt intervention on said subject by said physician based on the indication of ischemia to prevent further myocardial necrosis.

2. The method according to claim 1, wherein said calculating, by said processor, a HF value based on analyzing said HFQRS signal comprises calculating a HFQRS signal value by said processor.

3. The method according to claim 1, wherein said HF value is recorded for a plurality of different physiological states.

4. The method according to claim 1, wherein said physiological value is a heart rate.

5. The method according to claim 4, wherein:

said calculating, by said processor, a HF value comprises calculating, by said processor, a first HF value and calculating a second HF value; and said measuring, by said at least one electrode, at least one more physiological value comprises measuring, by said at least one electrode, a first physiological value associated with a time when said first HF value was measured and measuring, by said at least one electrode, a second physiological value associated with a time when said second HF value was measured.

6. The method according to claim 1, wherein said analyzing comprises one or more of:

producing, by said processor, a determination that ischemia is likely based on a non-positive value of said slope; and calculating, by said processor, a calculated value based on said HF value and said physiological value.

7. The method according to claim 6, wherein said plurality of points comprises points captured at a plurality of different heart rates.

8. The method according to claim 6, wherein:

said calculated value is a ratio of a current measured HFQRS signal RMS over a period of time, and a resting HFQRS signal RMS, measured in resting condition; and said physiological value is a ratio of a current measured HR over said period of time, and a resting HR, measured in resting condition.

9. The method according to claim 8, wherein said calculated value is equal to:

$$\frac{NHFRMS}{NHR} = \frac{(\max(HF) - \min(HF))}{((\text{current}_{HR}) - (\text{resting}_{HR}))}$$

wherein:

NHFRMS is a difference between a maximum current measured HFQRS signal RMS over said period of time, and a minimum HFQRS signal RMS, measured in resting condition;

NHR is a difference between said current measured HR over said period of time, and said resting HR, measured in resting condition;

Max(HF) is a maximal HF value measured during said time period;

Min(HF) is a minimal HF value measured during said time period;

$\text{current}_{HR}$ is a measurement of average HR over said period of time; and $\text{resting}_{HR}$ is an average HR measured in resting condition.

10. The method according to claim 1, wherein said physiological value is a normalized heart rate (NHR), wherein said NHR is a ratio of a measured HR over a first period of time, and a resting HR, measured in resting condition, over a second period of time.

11. The method according to claim 1, wherein said calculated value comprises a value based on dividing a first value of a measurement of said HF value by a second value of said HF value at rest.

12. The method according to claim 9, wherein said $\text{resting}_{HR}$ value is retrieved from storage, for said subject and/or for a category of subjects to which said subject is associated.

13. The method according to claim 1, wherein said physiological value is one or more of:

a. a measured breathing rate b. a value associated with a depth of breathing;

c. a tidal volume of breathing;

d. a measured breathing rate calculated by measuring intervals between R waves in consecutive QRS complexes.

14. The method according to claim 13, wherein said HFQRS signal value comprises one or more of:

a. a value based on measuring a Reduced Amplitude Zone (RAZ) in said HFQRS signal;

b. a ratio of a length of an interval between two adjacent local maxima of an envelope of said HFQRS signal and a length of the QRS complex;

c. a ratio of an area of a basin of the RAZ to an area of the HFQRS signal envelope;

d. is a ratio of a measured HFQRS signal value over a first period of time, and a resting HFQRS signal value, measured in resting condition, over a second period of time; and said physiological value is a ratio of a measured HR over said first period of time, and a resting HR, measured in resting condition, over said second period of time.

15. A system for analyzing an electro-cardiogram (ECG) or electrogram signal, the system comprising:

an input for an ECG or electrogram signal;

a high frequency (HF) signal extractor which extracts a HF portion in a frequency range of 150 Hz to 250 Hz from said ECG or electrogram signal; and a processor configured to:

calculate a HF value comprising an RMS of a HFQRS signal based on analyzing said HF portion;

measure at least one more physiological value associated with a subject;

analyze said ECG or said electrogram signal based on said HF value and said physiological value to determine whether said subject is ischemic, comprising:

produce a scatter plot of a plurality of points, each point defined by a pair of a first value of said HF value and a second value of said heart rate;

calculate a slope of a regression line passing through the plurality of points in the scatter plot; and determine a likelihood of ischemia based on said slope; and in response to said subject being ischemic, produce an indication of ischemia to a physician, to thereby perform prompt intervention on said subject by said physician based on the indication of ischemia to prevent further myocardial necrosis.

16. The system according to claim 15, wherein said physiological value is a heart rate.

17. The system according to claim 16, wherein said processor is configured to one or more of:

produce a scatter plot based on said plurality of points comprising points captured at a plurality of different heart rates;

calculate a calculated value based on said HF value and said physiological value.

18. The system according to claim 17, wherein said system is configured for performing one of more of:

a. displaying said scatter plot; and b. saving said HF value and said physiological value.

19. The system according to claim 17, and further comprising said apparatus-system configured for saving said calculated value.

* * * * *